(12) United States Patent
Noo

(10) Patent No.: US 8,139,709 B2
(45) Date of Patent: Mar. 20, 2012

(54) STAGGERED CIRCULAR SCANS FOR CT IMAGING

(75) Inventor: Frederic Noo, Midvale, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 42 days.

(21) Appl. No.: 12/560,396

(22) Filed: Sep. 15, 2009

(65) Prior Publication Data

US 2010/0135454 A1    Jun. 3, 2010

Related U.S. Application Data

(60) Provisional application No. 61/097,170, filed on Sep. 15, 2008.

(51) Int. Cl.
*G01N 23/083* (2006.01)
*H05G 1/02* (2006.01)
*A61B 6/03* (2006.01)

(52) U.S. Cl. ............................................. 378/9; 378/19
(58) Field of Classification Search ................ 378/4–20, 378/91, 92, 210
See application file for complete search history.

(56) References Cited

U.S. PATENT DOCUMENTS

| | | | |
|---|---|---|---|
| 4,196,352 A | 4/1980 | Berninger et al. | |
| 6,421,412 B1 | 7/2002 | Hsieh et al. | |
| 6,760,399 B2 | 7/2004 | Malamud | |
| 6,763,081 B2 | 7/2004 | Tam | |
| 6,778,630 B2 | 8/2004 | Silver et al. | |
| 7,062,006 B1 | 6/2006 | Pelc et al. | |
| 7,197,106 B2* | 3/2007 | Hartung et al. | 378/19 |
| 7,269,244 B2 | 9/2007 | Tang et al. | |
| 7,324,623 B2 | 1/2008 | Heuscher | |
| 7,403,587 B2 | 7/2008 | Bontus et al. | |
| 7,473,901 B2* | 1/2009 | Scholz | 250/363.08 |
| 2008/0123803 A1 | 5/2008 | De Man et al. | |

FOREIGN PATENT DOCUMENTS

WO    WO 92/03092    3/1992

* cited by examiner

*Primary Examiner* — Anastasia Midkiff
(74) *Attorney, Agent, or Firm* — James W. Hill; M. Todd Hales; McDermott Will & Emery, LLP

(57) ABSTRACT

Certain embodiments provide staggered circular scans for CT imaging. In certain embodiments, a CT imaging system comprises a plurality of source-detector assemblies that are axially offset from one another and rotate about a rotation axis to provide staggered circular CT scanning.

18 Claims, 21 Drawing Sheets

STAGGERED CIRCULAR SCANS WITH THREE SOURCES

STAGGERED CIRCULAR SCANS WITH FOUR SOURCES

STAGGERED CIRCULAR SCANS WITH TWO SOURCES

STAGGERED CIRCULAR SCANS WITH THREE SOURCES

STAGGERED CIRCULAR SCANS WITH FOUR SOURCES
3D VIEW

LATERAL VIEW

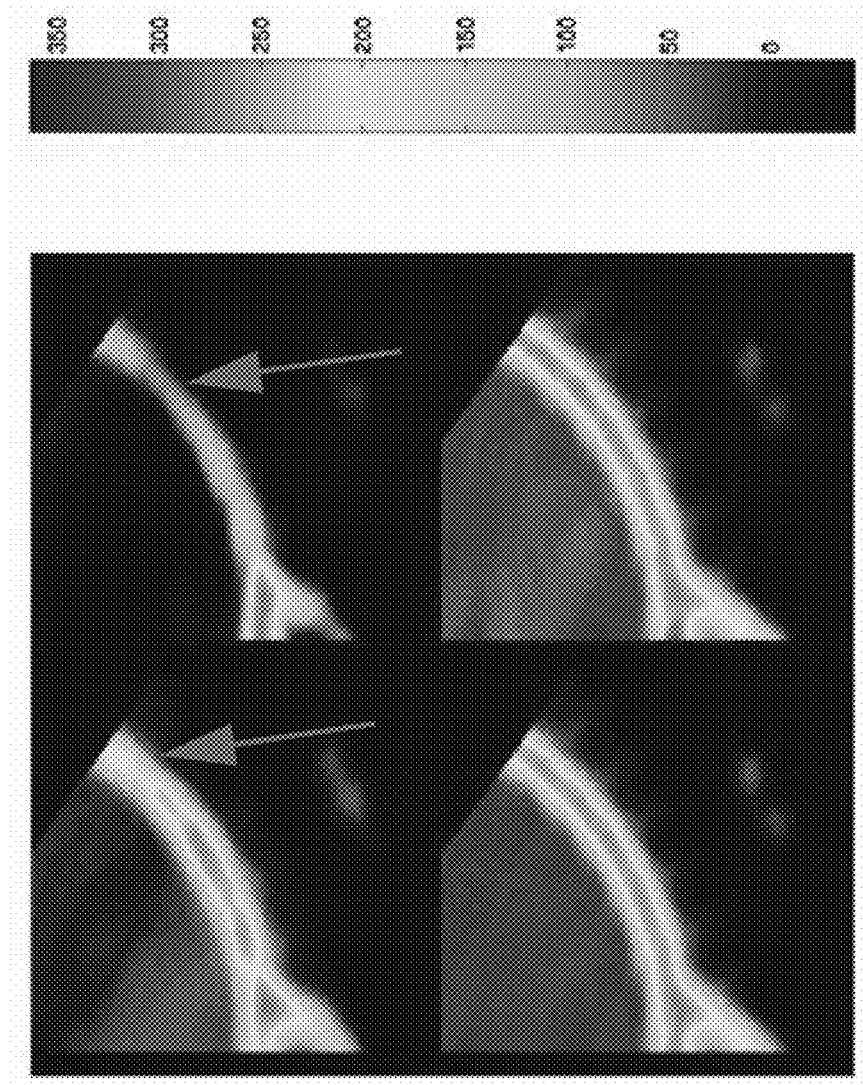
Fig. 10
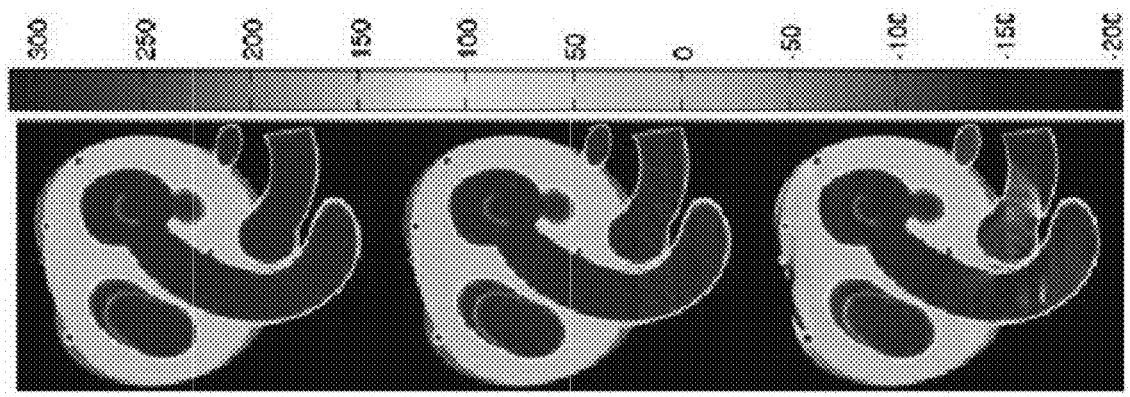

STAGGERED CIRCULAR SCANS FOR CT IMAGING

RELATED APPLICATION

The present application claims the benefit of priority under 35 U.S.C. §119 from U.S. Provisional Patent Application Ser. No. 61/097,170, entitled "STAGGERED CIRCULAR SCANS FOR CT IMAGING," filed on Sep. 15, 2008, which is hereby incorporated by reference in its entirety for all purposes.

FIELD OF THE INVENTION

The present disclosure relates to computed tomography (CT) imaging.

BACKGROUND OF THE INVENTIONS

X-ray computed tomography has become a prominent tool for cardiac imaging due to the introduction of multislice computed tomography. This prominence has grown progressively with successive breakthroughs in volume coverage and temporal resolution. One example of a multislice CT is the Aquilion ONE by Toshiba. As designed, the Aquilion ONE allows imaging of the entire heart within a single heartbeat using a circular scan with a wide cone angle that axially covers 16 cm at a rotation speed of 350 ms per turn. Toshiba's technology progresses are followed closely by Philips that advertises a 128-row commercial product with a rotation speed of 250 ms per turn (The Ovation, from the Brilliance iCT line) and that also advertises a 256-row prototype scanner.

SUMMARY OF THE INVENTIONS

A major problem with wide-cone-angle circular scans is the issue of cone-beam (CB) artifacts. A lack of tomographic information in the circular scan is at the root of these artifacts. This lack of information prevents accurate reconstruction outside the plane of the source trajectory with a magnitude that quickly increases with the distance from this plane. Moreover, for coronary CT angiography (CTA), the problem is worsened by the need to restrict the data acquisition to a short-scan (240 degrees) to properly freeze the motion of the heart.

One approach to mitigate CB artifacts is to complement the circular scan with measurements on a line or a helix. However, this approach suffers from the physical incapacity to collect all measurements, circular and complementary, within the same heartbeat. Another approach to mitigate CB artifacts is to perform data acquisition with a source trajectory that is complete such as a helix or a saddle, and thus allows accurate reconstruction. This approach is practical but suffers from high costs because axial motion of the source relative to the patient cannot be achieved using conventional patient translation, given that 16 cm is to be covered in 180 ms or so.

In accordance with embodiments of the present inventions, staggered circular scans for CT imaging are provided.

In certain embodiments, a CT imaging system comprises a plurality of x-ray sources configured to rotate about an rotation axis, the x-ray sources each generating a beam of radiation, at least two of the plurality of x-ray sources being angularly offset from each other at discrete locations around the rotation axis and being axially offset from each other along the rotation axis. The CT imaging system also comprises a plurality of x-ray detectors configured to rotate about the rotation axis in a rotation direction, each detector situated opposite an associated one of the plurality of x-ray sources and having (i) a curvilinear long axis oriented along the rotation direction, and (ii) a short axis that is transverse to the long axis, at least two of the plurality of detectors being angularly offset from each other at discrete locations around the rotation axis and being axially offset from each other along the rotation axis, wherein adjacent edges parallel to the short axes of the at least two angularly offset x-ray detectors are not substantially spaced apart from each other.

In certain embodiments, a CT imaging system comprises a plurality of x-ray sources configured to rotate about an rotation axis, the x-ray sources each generating a beam of radiation, the plurality of x-ray sources being axially offset from one another along the rotation axis. The CT imaging system also comprises a plurality of x-ray detectors configured to rotate about the rotation axis in a rotation direction, each detector situated opposite an associated one of the plurality of x-ray sources and having a curvilinear long axis oriented along the rotation direction, wherein axially adjacent x-ray sources of the plurality of x-ray sources along the rotation axis are angularly offset from each other by 60 degrees or less.

It is to be understood that both the foregoing general description and the following detailed description are exemplary and explanatory and are intended to provide further explanation of the inventions as claimed.

BRIEF DESCRIPTION OF THE DRAWINGS

FIG. 10 shows reconstruction results from a circular scan in Aquilion ONE geometry.

DETAILED DESCRIPTION OF THE INVENTION

Figure 1:
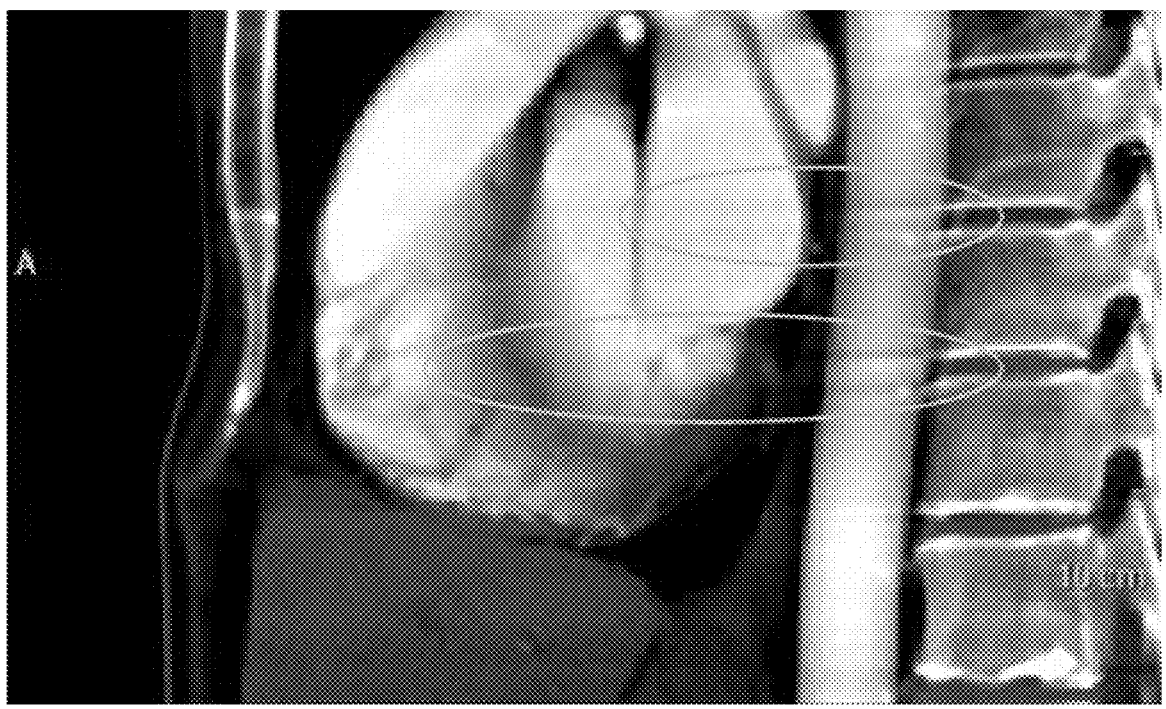
FIG. 1 shows cone beam (CB) artifacts in a CT scan obtained in the helical mode.

Cone beam (CB) tomography is the process of reconstructing a function in the three dimensional space from CB projections. Let $\mu$ denote this function. By definition, a CB projection is the set of line integrals of $\mu$ along the lines that diverge from a point in space, called the vertex point. CB projections may be measured on various sets of vertex points. Here, the discussion is restricted to projections measured while the vertex point moves along a path in space called the vertex path. In x-ray CB tomography, $\mu$ is the linear x-ray attenuation coefficient within the patient, and the vertex point and the vertex path are, respectively, the position and the trajectory of the x-ray source relative to the patient. For staggered circular scans, the vertex path comprises of a number of parallel circles (or segments of circles), each created from an individual x-ray source and detector assembly.

Accuracy of reconstruction is a primary concern in tomography. Accurate reconstruction is deemed achievable when a reconstruction algorithm can be devised such that (i) the reconstruction is consistent, in that it would be the true function $\mu$ if the spatial and temporal resolution were not limited and the data was perfect, and (ii) the reconstruction is stable in the sense that it is robust for both finite resolution effects and data imperfections. Not all data acquisition geometries allow accurate reconstruction. Accurate reconstruction at a given location is enhanced when all planes through this location intersect the source trajectory, which is Tuy's condition. If Tuy's condition is not satisfied, accurate reconstruction is not possible. CB tomography with a circular source trajectory suffers from this problem for reconstruction outside the trajectory plane. Stable reconstruction can be performed with the FDK algorithm but this reconstruction is not consistent and any attempt to make it consistent inevitably ruins stability. Basically, the circular trajectory does not provide enough information for reconstruction outside the trajectory plane, and the amount of missing information worsens when using a short-scan (less than 360 degrees) for reconstruction. Image artifacts due to data insufficiency are called CB artifacts.

Cardiac CT imaging is currently performed with CT scanners equipped with either one or two x-ray sources and with a number of detector rows varying between 32 and 64. Most scanners offer two data acquisition modes: sequential circular scanning and helical scanning. Until recently, the former scanning mode was only used for calcium scoring, while the latter scanning mode was preferred for coronary CTA.

Coronary CTA using helical data acquisition proceeds as follows. First, CB projections of the heart are collected over several turns of a helix using continuous patient translation. Second, a slow-motion phase of interest in the heart cycle is selected. Third, short-scan segments (typically 240 degrees) of the obtained helical CB data are subsetted using the electrocardiogram (ECG), with each segment centered on the selected heart phase. Lastly, an axial slab of the heart is reconstructed from each subsetted short-scan segment of data and, from there, a volumetric reconstruction of the entire heart in the selected phase is obtained by combining the slabs together.

In the sequential mode, data acquisition proceeds using the step-and-shoot approach as follows. First, CB circular scans are collected for a number of patient bed positions covering the axial extent of the heart. Second, all circular scans are centered on the same phase in the heart cycle and yield a reconstruction of an axial slab of the heart in this phase. Third, a volumetric reconstruction of the entire heart in the selected phase is obtained by combining the slabs together.

In both data acquisition modes, high temporal resolution is needed to mitigate motion artifacts within each slab, and a high number of detector rows allows reconstructing thicker slabs. Since each slab corresponds to a different heartbeat, the thicker the slab the smaller the number of heartbeats involved in the imaging process. Involving fewer heartbeats helps in reducing motion artifacts due to heartbeat arrhythmia and in decreasing the amount of contrast agent that must be continuously injected to mitigate spurious inhomogeneities in the heart reconstruction. High temporal resolution within the slabs is obtained using fast rotation speeds and/or an increase in the number of x-ray tubes.

In practice, care has to be taken about CB artifacts as much as motion artifacts because each short-scan violates Tuy's condition for reconstruction of its associated slab and the problem unfortunately increases with the axial thickness of the slab. The helical mode fares better than the sequential mode in terms of CB artifacts. This advantage comes from the availability of measurements outside the subsetted short-scans. When used wisely, these measurements allow a reduction in both CB and motion artifacts without affecting much the temporal resolution. However, these measurements are costly in terms of dose. Prospective ECG gating has been suggested to reduce the tube current outside the subsetted short-scans and thereby reduce dose. But, in the clinical environment, heartbeat arrhythmia has prevented effective use of such gating, and furthermore has led to using a low, dose-detrimental helix pitch, so that coronary CTA in the helical mode remains a high dose procedure at a level that may be acceptable in comparison with cardiac catheterization, but not with a conventional CT scan. Coronary CTA in sequential mode is more attractive than in the helical mode in terms of dose because prospective gating is more easily handled in this mode. Indeed, assume a scenario where a sudden heartbeat variation occurs when not expected. In this scenario, prospective gating would likely result in data for (at least) one of the axial slabs to be collected away from the desired heart phase, over a fast-moving portion of the heart cycle. In helical mode, the implications of such a situation are dramatic because data acquisition for the given slab cannot be repeated since the patient bed moves continuously. In contrast, in the sequential mode, the situation is controllable. Not only can the data acquisition be repeated but it can also first be interrupted because the instruction to move the bed can be postponed until a signal has been given that data acquisition at a given bed position is successful. The dose advantage of the sequential mode comes however at a cost of increased sensitivity to CB artifacts, to heartbeat arrhythmia, and also to contrast wash-out because there is no complementary data and at least one heartbeat has to be skipped during translation of the patient bed from one position to the next. Nevertheless, warranted concerns about the high radiation dose of CT have recently led many institutions to using the sequential mode rather than the helical mode.

Cone-beam artifacts have had little impact on image quality for scanners with 32 to 64 rows. But they become quickly prominent as the cone angle is increased, as demonstrated in FIG. 1. FIG. 1 shows CB artifacts in a cardiac CT result obtained in helical mode with 128 detector rows covering 8 cm. Artifacts radiating from the spine through the aorta and then the heart are clearly seen in this result.

Figure 2:
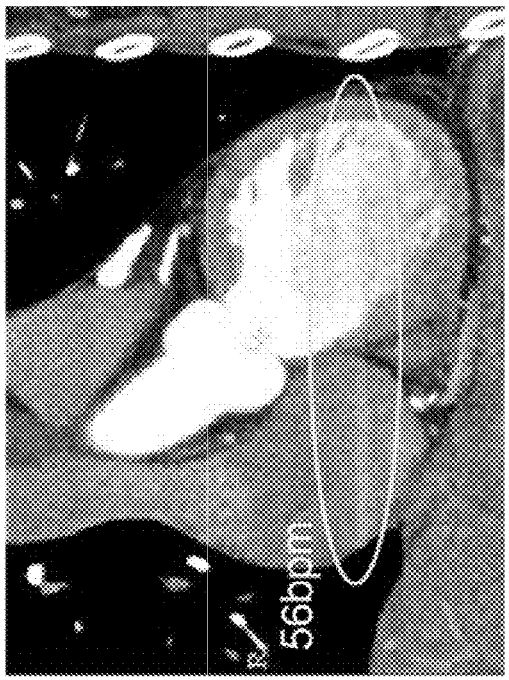
FIG. 2 shows three helical cardiac scan images.
Figure 2:
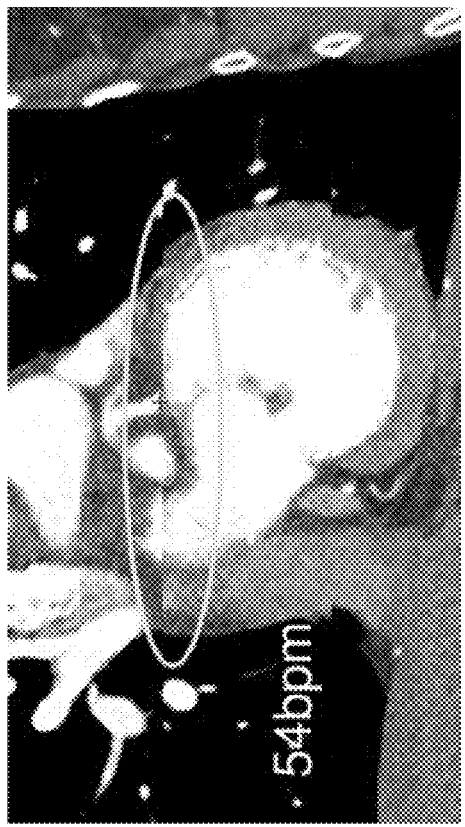
Figure 2:
Figure 3:
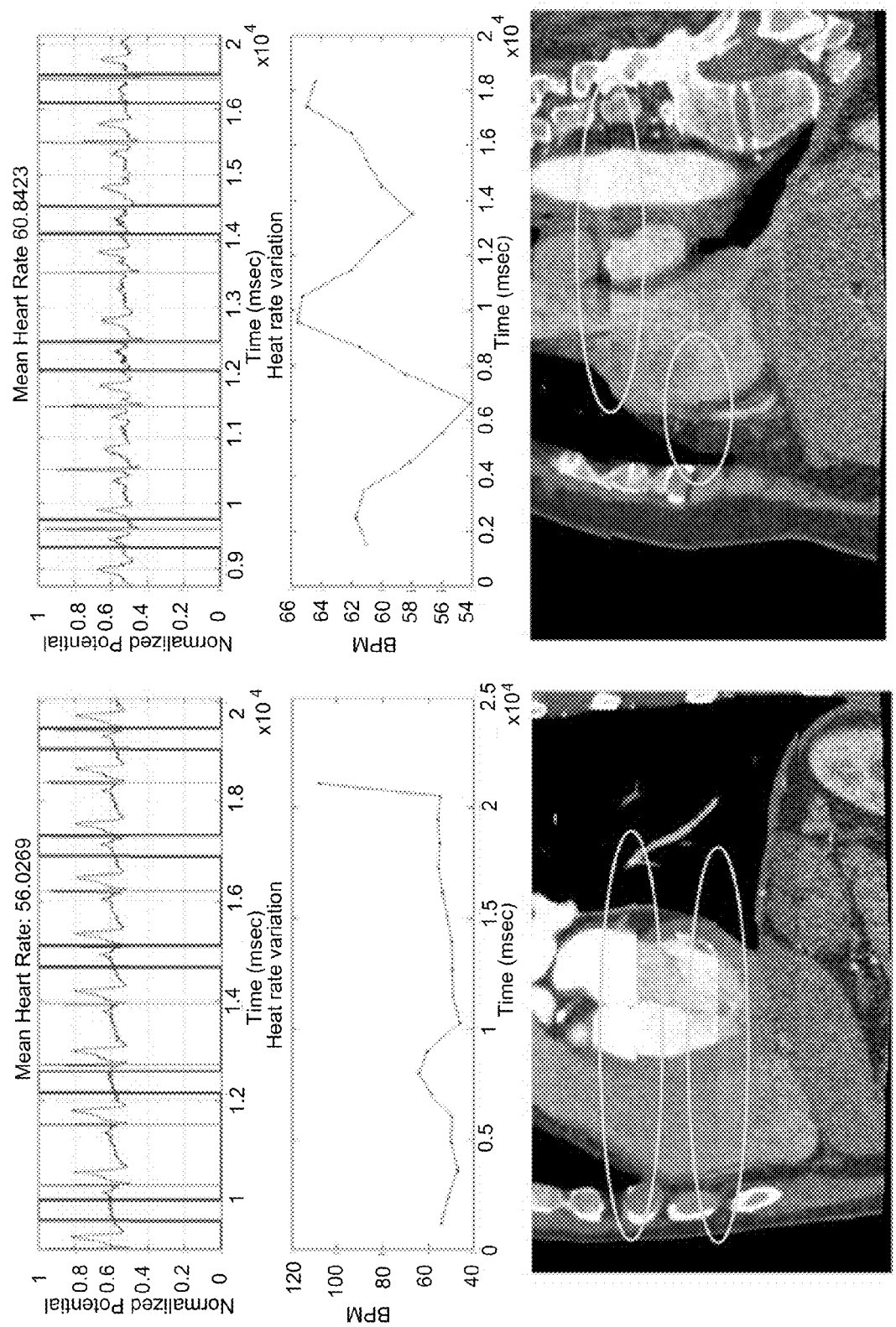
FIG. 3 shows two sequential scan images.

FIGS. 2 and 3 show cardiac imaging results obtained using helical scans and also sequential scans on the Philips Brilliance 64, respectively. All displayed results correspond to fairly low heartbeat rates and thus primarily show the effects of beat-to-beat variability and contrast wash-out on image quality. FIG. 2 shows three helical cardiac scan results obtained on the Philips Brilliance 64 with different patients, each having a different heartbeat rate expressed in beats per minute (bpm). FIG. 3 shows two sequential results obtained on the Philips Brilliance 64 with different patients. The red lines in the ECG record show when the x-rays were turned on and off. The green lines show the detected R-tags.

Figure 4:
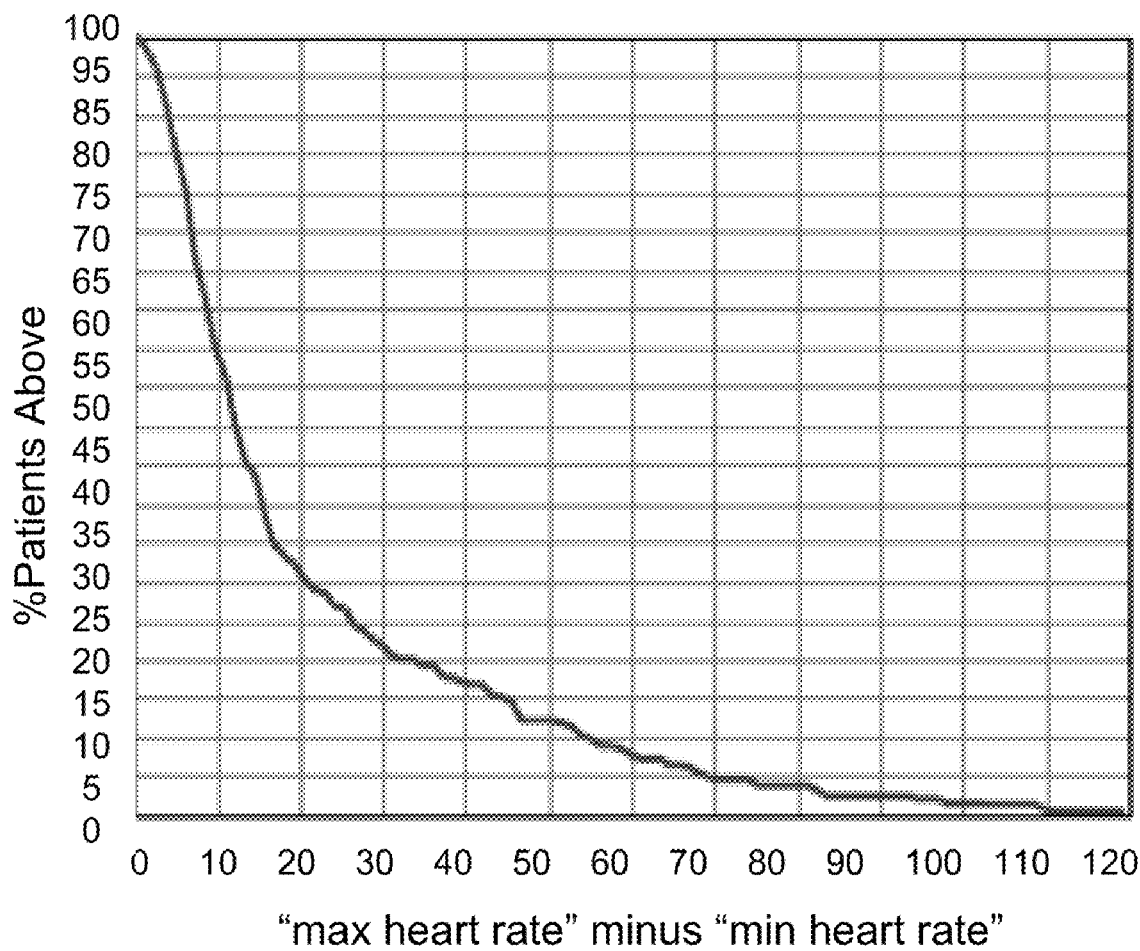
FIG. 4 is a graph relating the maximum variability in heartbeat rate over the scan duration to the percentage of patients that exhibits at least this variability in a database of 245 patients.

First, the comparison of results in FIGS. 2 and 3 illustrates that statement above about image quality being inferior in sequential mode. Second, the results in FIG. 3 show that significant artifacts even appear with small fluctuations in the heartbeat rate. Moreover, as illustrated in FIG. 4, such fluctuations are fairly common in practice. FIG. 4 shows a graph relating the maximum variability in heartbeat rate over the scan duration to the percentage of patients that exhibits at least this variability in 245 patients who underwent a cardiac CT scan with beta blockers. For instance, the graph shows that 60% of the patents had variations larger than 10 in their heartbeat rate (measured in beats per minute) during scanning time.

In general, beat-to-beat variability may be expected, despite the use of beta blockers because the injection of the contrast agent typically generates anxiety in the patient just before the scan is started. The results in FIGS. 2, 3 and 4 show the need for cardiac imaging within a single heartbeat.

A goal of embodiments of the present inventions is to simultaneously achieve one or more of the following advantages:

(i) Independence of image quality from beat-to-beat variability so that patients with arrhythmia may be scanned very accurately. Currently, even the dual source system has limitations with arrhythmia.

(ii) Elimination of artifacts due to rapid wash-out of the contrast agent, with uniform high contrast enhancement over the entire heart, which is utilized for the detection of stenoses.

(iii) No need of beta blockers since beat-to-beat variability is not a concern.

(iv) Significant reduction in the amount of injected contrast agent since the exam is much faster.

(v) Less (if any) motion artifacts due to breathholding and swallowing. Swallowing and respiratory motion cause artifacts as the heart contracts, and breathholding causes acceleration of the heart rate.

(vi) Reduction of dose to that of a conventional CT scan.

(vii) Opening of cardiac CT to a wider population of patients who otherwise would be ruled out or may not even be referred for a CT scan by their physician due to the absence of the advantages that were just listed.

(vii) Opening of new applications, such as cardiac CT perfusion.

As discussed above, CT manufacturers have been actively working on increasing the number of detector rows so as to precisely allow scanning the entire heart in a single heartbeat. At this stage, data acquisition is focused on circular scanning because this motion is the simplest to implement. However, the CT manufacturers are aware of CB artifacts that occur with circular scanning and their deleterious impact on image quality, especially at the required cone angle.

Figure 5:
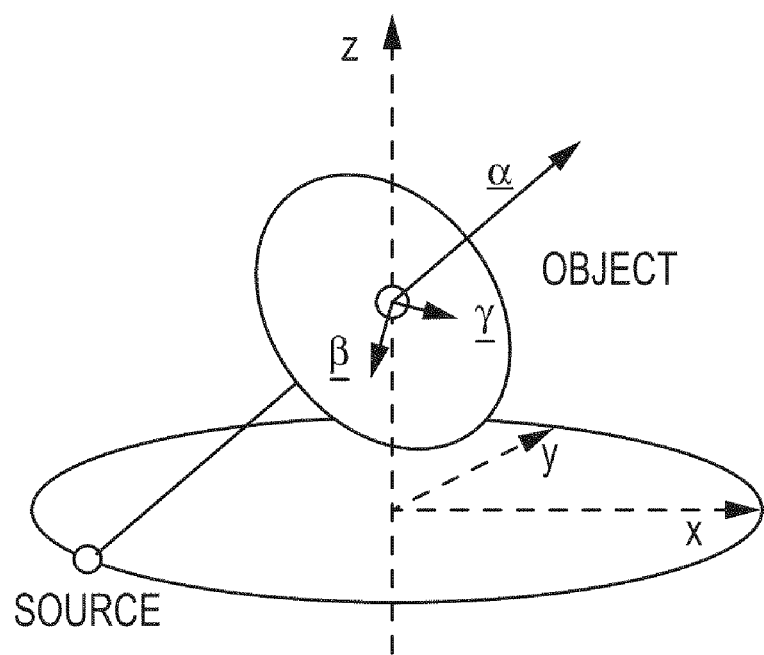
FIG. 5 shows Fourier transform information from a one source position.

The purpose of the following discussion is to quantify the amount of incomplete data in a circular scan so that the issue of CB artifacts may be better appreciated. A convenient way to quantify the data incompleteness is to use the concept of local Fourier analysis. That is, we evaluate how much Fourier information is available for reconstruction of a small object placed at an arbitrary location. The size of this object is assumed to be small enough so that the divergence of the beam may be neglected or, in other words, so that the CB measurements through it may be viewed as 2D parallel-beam projections. Each source position yields one parallel-beam projection and, thus, by application of the Fourier slice theorem, yields the Fourier transform of the object on one plane in space, namely $$(F\mu)(\nu 1\beta + \nu 2\gamma) \text{ with } (\nu 1, \nu 2) \in \mathfrak{R}$$

where $\beta$ and $\gamma$ are orthogonal unit vectors perpendicular to the line of direction $\alpha$ that connects the object to the source, as depicted in FIG. 5. FIG. 5 shows Fourier transform information for one source position. In FIG. 5, the black dot is the object and the shaded area delineates the plane where the Fourier transform of the object is known from the measurements at the given source position.

Figure 6:
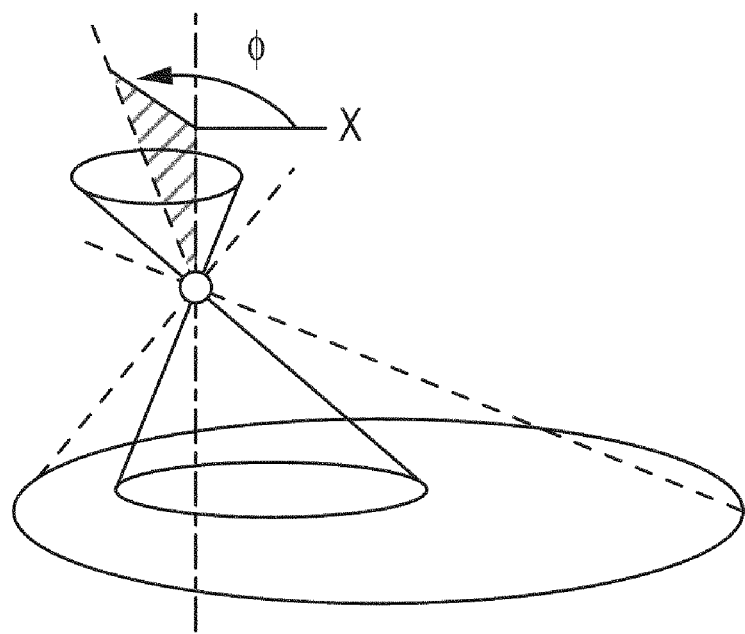
FIG. 6 illustrates a cone of missing frequencies for an object placed off the rotation axis.
Figure 7A:
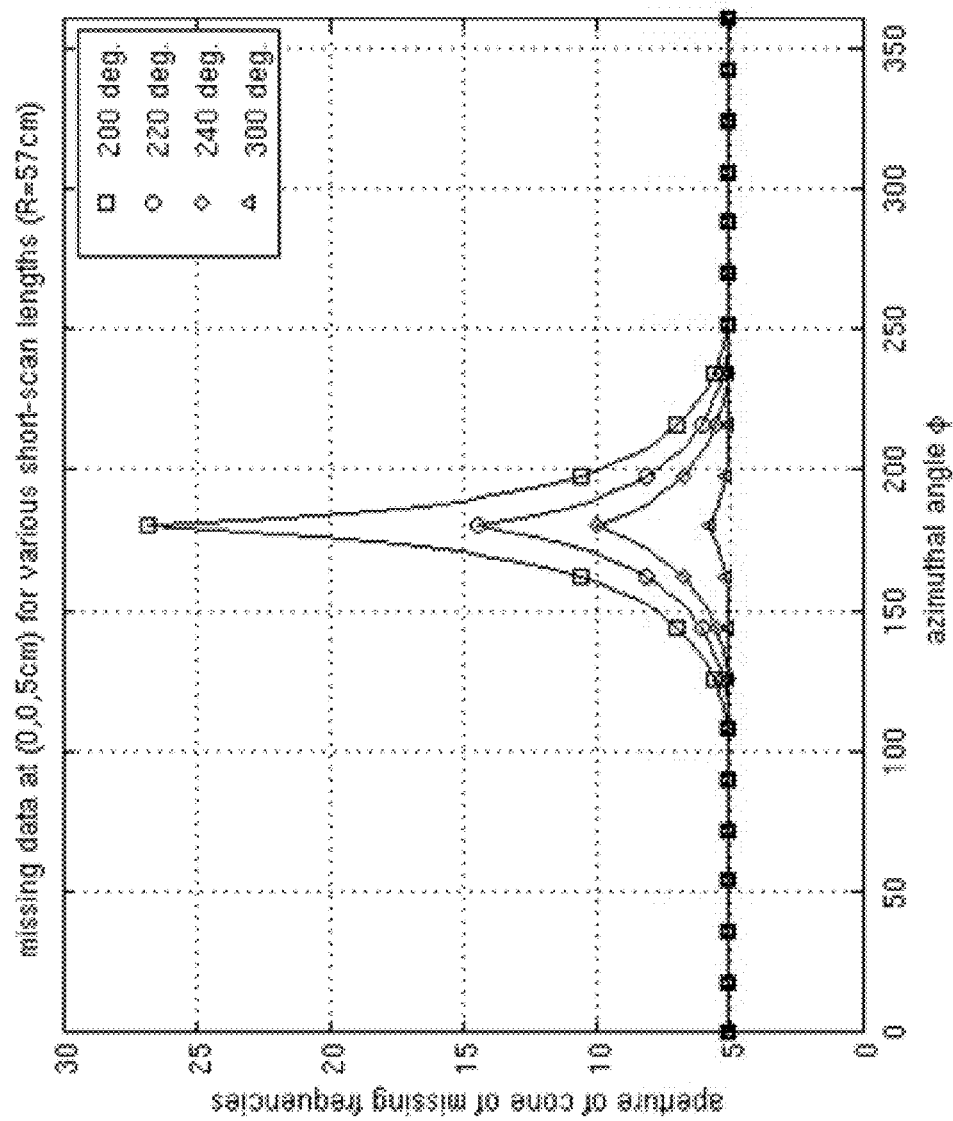
FIG. 7 are graphs showing the cone of missing frequencies for various object placements and various data-acquisition ranges.
Figure 7B:
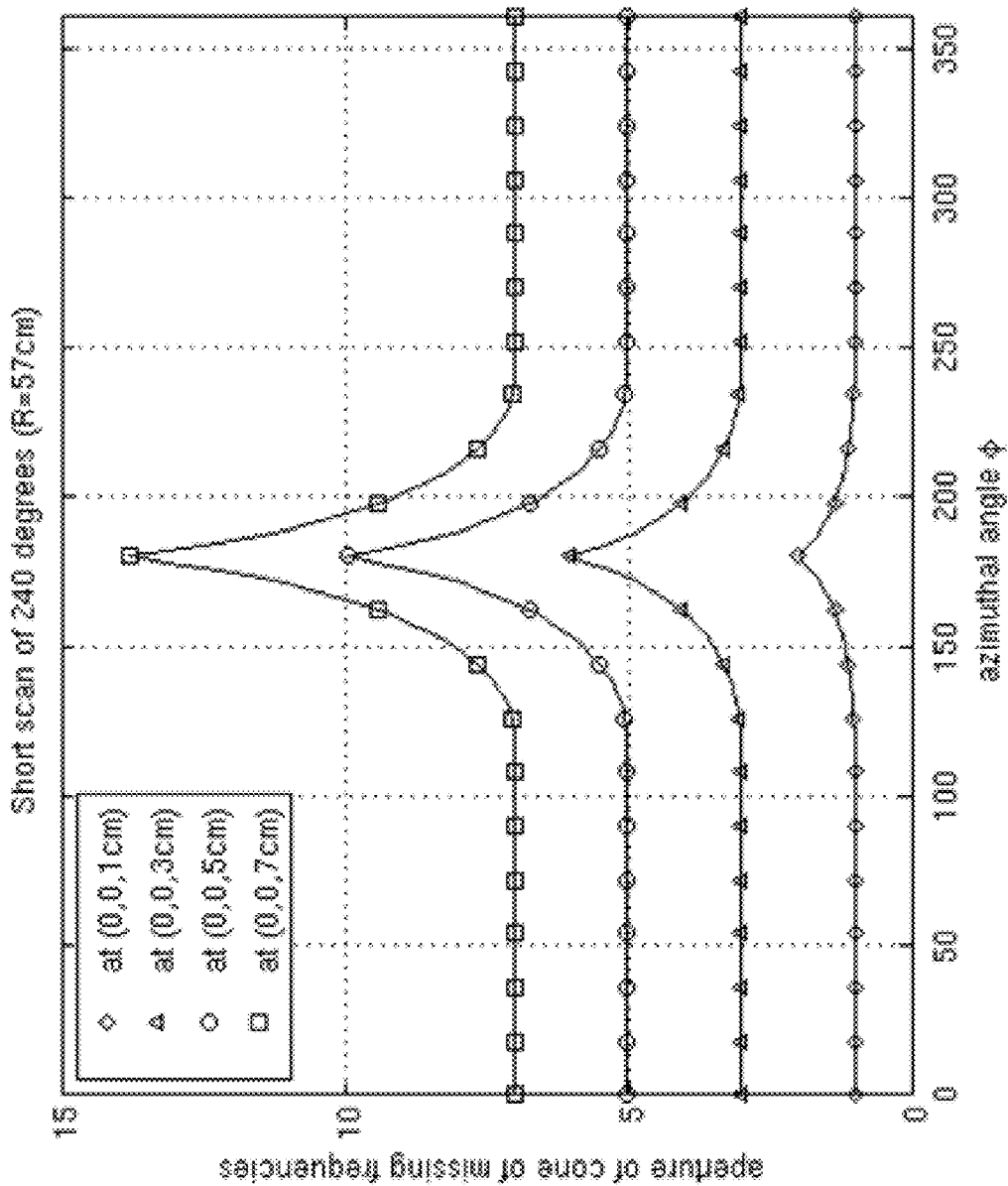
Figure 7C:
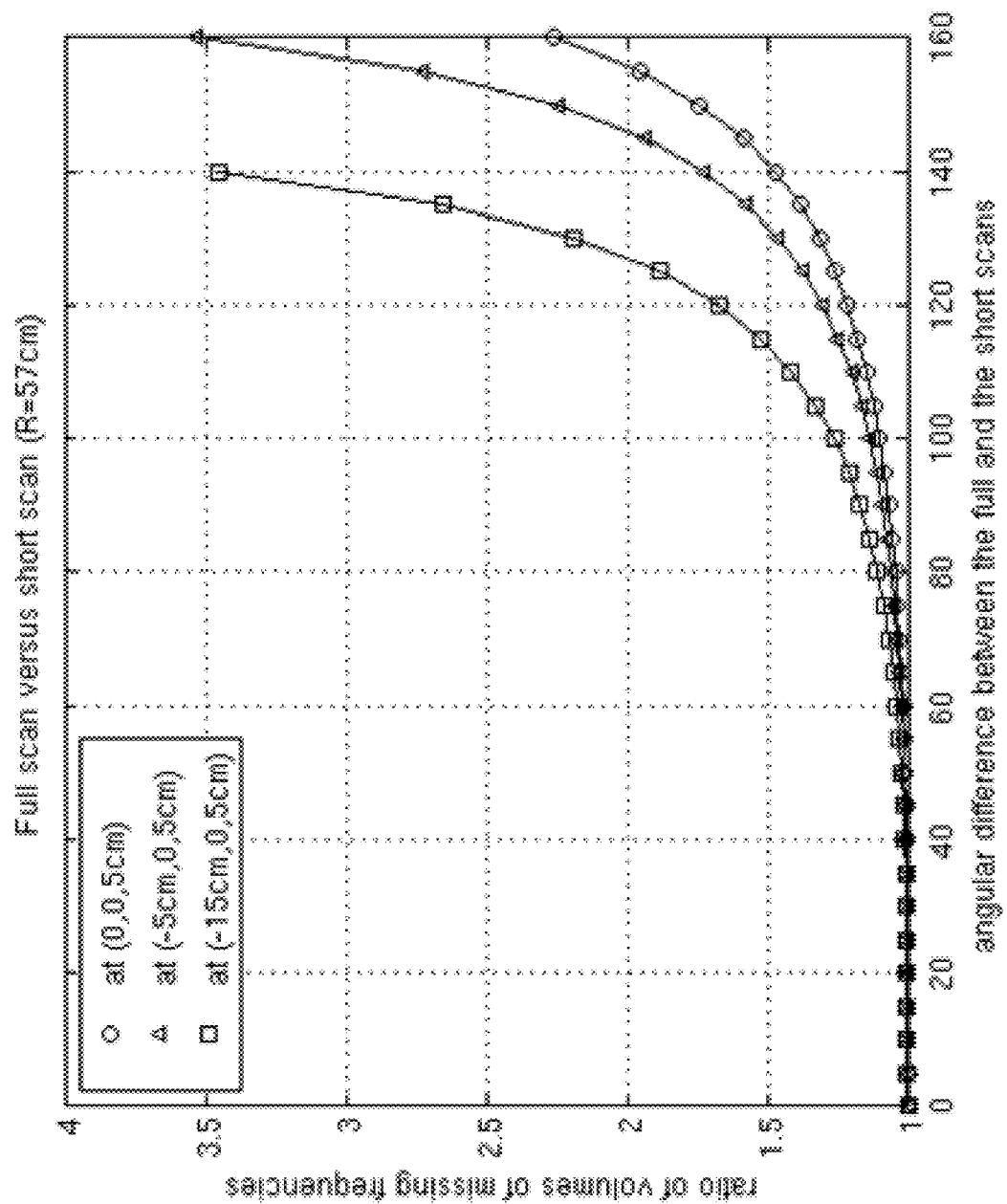
Figure 7D:
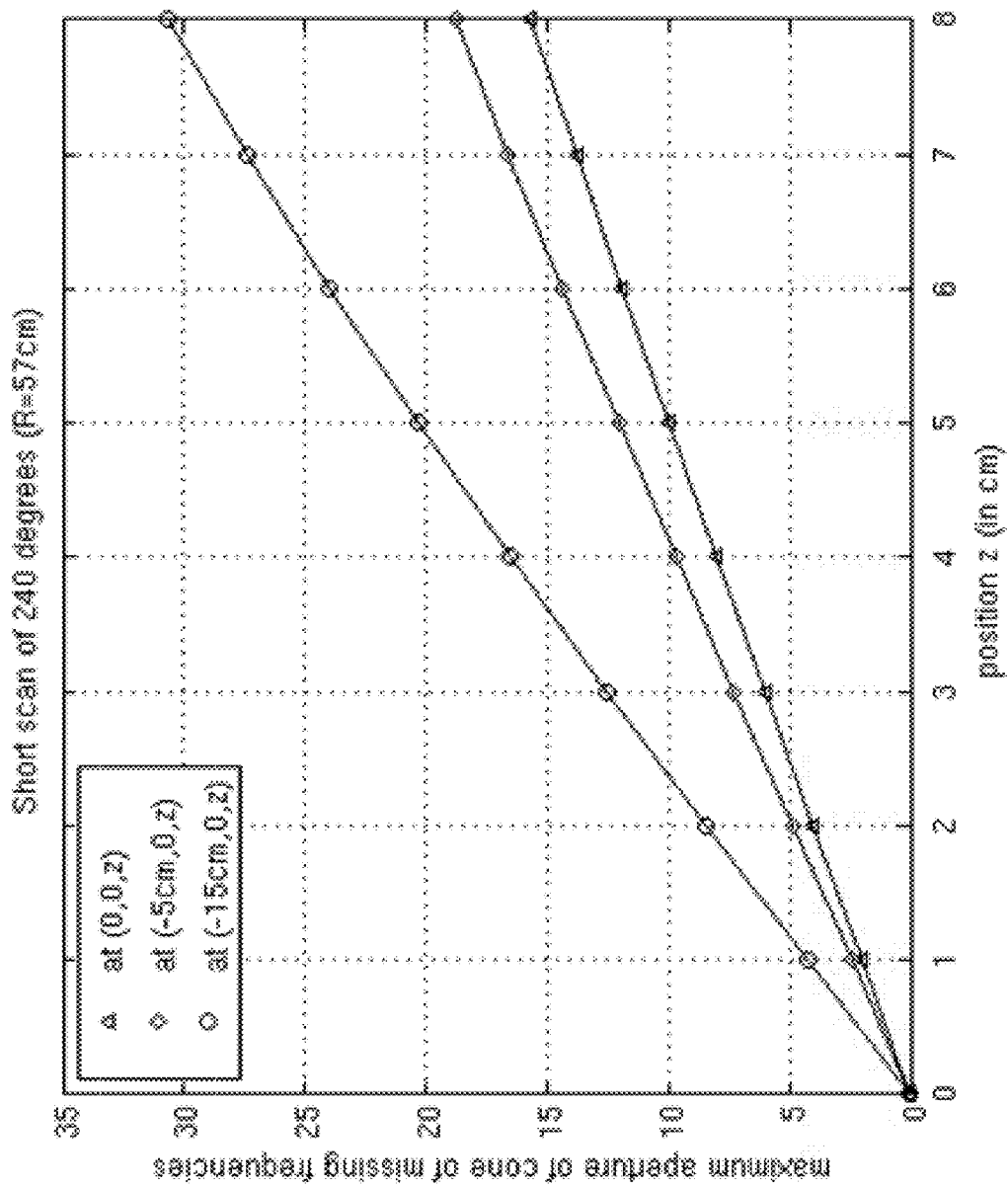

When the union of the Fourier planes obtained by considering all source positions covers the entire Fourier domain, the data is complete for reconstruction of the small object, otherwise the data is incomplete. In circular CB tomography, the only object placement yielding complete data is in the plane of the source trajectory. Outside this plane, there is always a cone of missing frequencies in the Fourier domain, as shown in FIG. 6, and this situation makes the circular CB reconstruction problem there equivalent to the limited-angle problem of 2D tomography. FIG. 6 illustrates the cone of missing frequencies for an object placed off the rotation axis assuming a 360-degree data acquisition. The aperture of the cone is measure at each angle $\phi$. As illustrated in FIG. 6, the aperture of the cone relative to the -axis generally varies with the angular position $\phi$ around this axis.

The graphs in FIG. 7 quantify the magnitude of the cone of missing frequencies for various object placements and data acquisition ranges for a conventional circular source trajectory of radius 57 cm. For these plots, the short-scans were always centered on the point (0, 0, 57 cm). The top-left graph shows how the cone aperture varies with $\phi$ for four different data acquisition ranges, assuming that the object is on the -axis at 5 cm from the source-trajectory plane. The top-right graph shows how the cone aperture varies with $\phi$ for four different object placements on the -axis, assuming that the data acquisition is performed over a short-scan of 240 degrees. Note that reconstruction is usually performed from short scans of 240 degrees in coronary CTA. The bottom-left graph shows how the volume of missing frequencies increases with reduction in the data acquisition range. And lastly, the bottom-right graph shows how the maximum aperture of the cone of missing frequencies increases with the distance from the source-trajectory plane. The following conclusions can be made from these graphs: (i) using a short scan instead of a full scan significantly increases the data incompleteness, (ii) data incompleteness quickly increases with the distance from the source trajectory plane, and (iii) for coronary CTA, where the region-of-interest is at most 7.5 cm away from the -axis, a short scan of 240 degrees is a good compromise between data incompleteness and temporal resolution. As a side observation, note that data truncation issues are not included in local Fourier analysis and can further increase the amount of data incompletion.

From the discussion above, we wish to emphasize that CB artifacts in circular CB tomography are not the result of a weakness from the reconstruction algorithm, but rather from an inherent fault of the data acquisition, which simply does not provide complete Fourier information. Some algorithms may be designed to perform better than others, such as the factorization method, which we have recently developed and will use in this research. However, there is an intrinsic limit to how well the algorithm can perform, and reducing the cone angle is the only way to improve on this limit.

Cardiac disease remains the leading cause of death in western civilization, and cardiac CT imaging has definitely shown that it can play a significant role in the diagnosis and prevention of heart diseases. Embodiments of the present inventions provide another forward leap in cardiac CT technology so that accurate coronary CTA can be achieved consistently and with a dose comparable to that of a conventional CT scan. Moreover, embodiments of the present inventions also increase the diagnostic strength of CT imaging by allowing more accurate perfusion imaging of various body regions such as the heart, the liver, and in particular the head, where CB artifacts from a circular orbit is a severe problem.

In certain embodiments of the present inventions, CB artifacts are mitigates by using (i) staggered circular scans that use several x-ray sources together to obtain CB data on parallel circular trajectories for the net effect of reducing the cone angle without requiring axial motion, and (ii) innovative reconstruction algorithms that draw on recent advances in image reconstruction theory. Staggered circular scans may be defined with an index K that gives the number of x-ray sources involved.

A body of knowledge can be built around staggered circular scans for the selection and optimization of orientations and constructions of staggered circular scans, and building this body of knowledge will achieve the one or more of following aims:

Aim 1. Development, implementation and validation of a preferred reconstruction algorithm for accurate coronary CTA using staggered circular scans of index K=2, K=3 and K=4.

Aim 2. Comparative evaluation of staggered circular scans against each other and against the conventional circular data acquisition. This aim will use computer simulations. The comparison focuses on (i) required detector area, (ii) spatial resolution and noise, (iii) dose, (iv) scatter characterization for a number of anti-scatter grids, (v) ability to detect stenosis in the coronary arteries. This last figure-of-merit will be quantified in part using ROC-based human observer studies. The dose and scatter evaluations will be achieved using Monte-Carlo simulations.

Aim 3. Demonstration of robustness for real data: The goal here is to show that the reconstruction algorithm of Aim 1 is robust for real data. This will be performed in part using ROC-based human observer studies with data from an anthropomorphic phantom collected on a commercial CT scanner.

Aim 4. Feasibility demonstration of accurate general body imaging with a scanner designed to perform staggered circular scans:

A new source-detector arrangement can be used for a scanner to perform staggered circular scans, and this new arrangement prevents or limits conventional helical data acquisition and reconstruction. A major strength of current CT systems is their versatility (cardiac CT is only one of many diagnostic applications of CT). A reconstruction algorithm can be used to perform a preliminary (subjective) evaluation with real data from an anthropomorphic phantom.

Staggered circular scanners according to various embodiments of the present inventions will now be described with references to FIGS. 8a-8d.

Figure 8A:
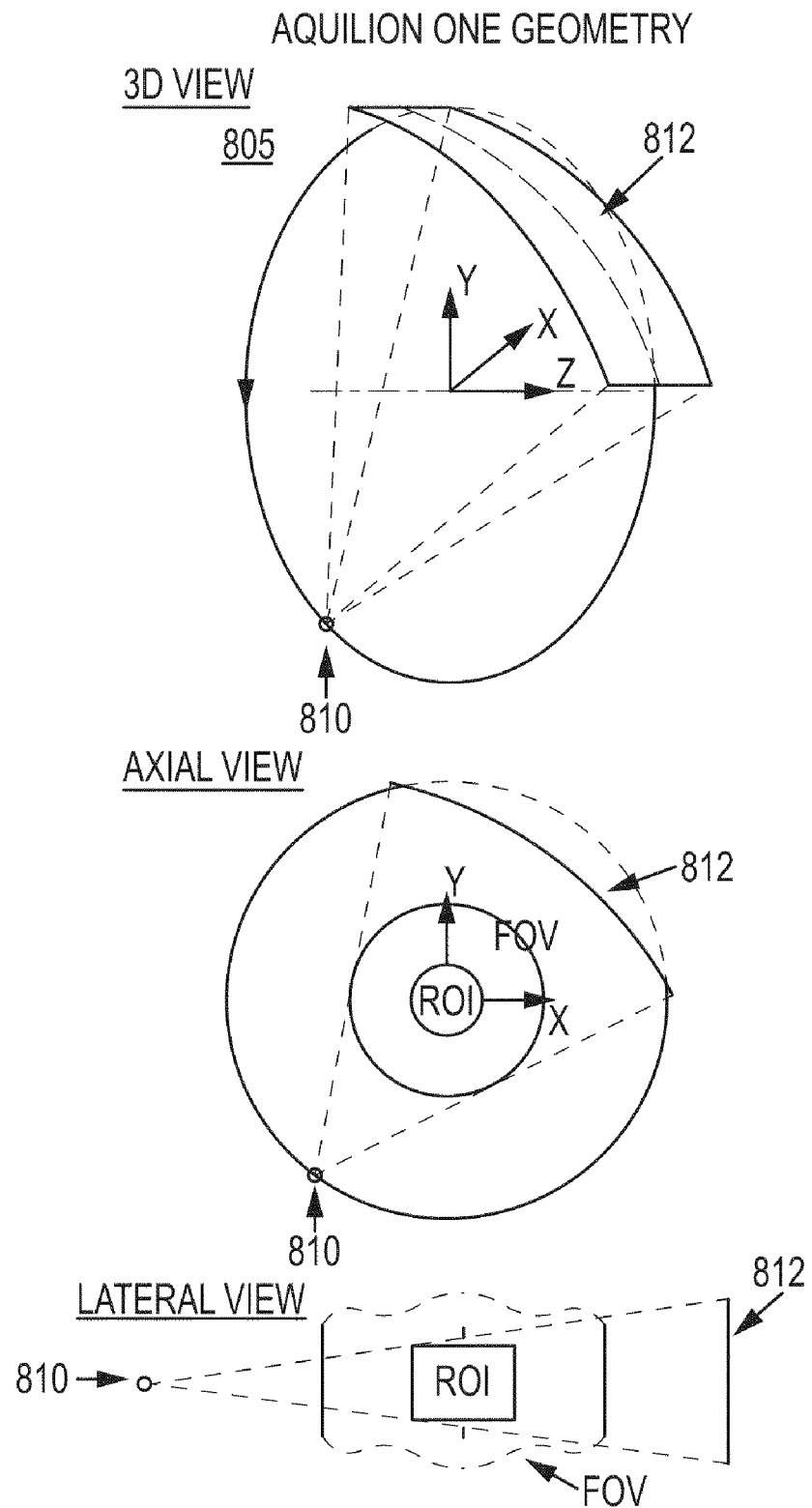
FIG. 8a shows a circular scanner with one source.
Figure 8B:
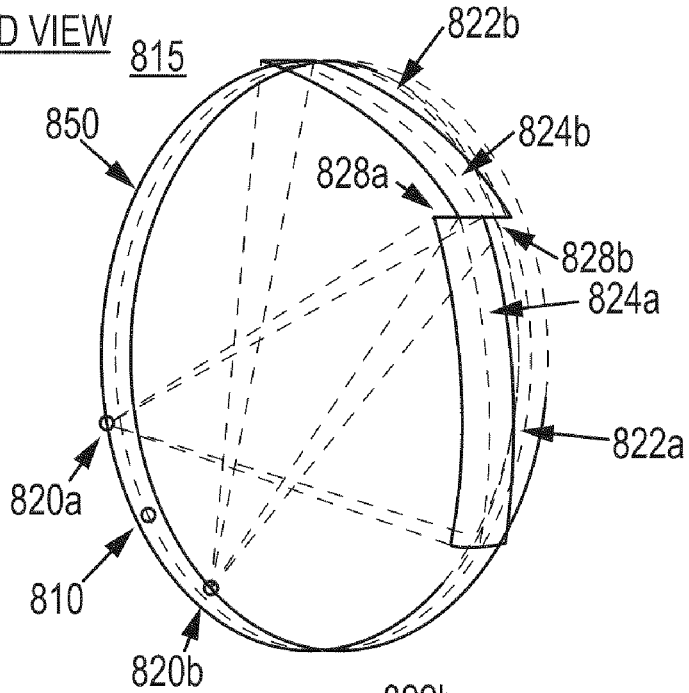
FIG. 8b shows a staggered circular scanner with two sources according to an embodiment of the present inventions.
Figure 8B:
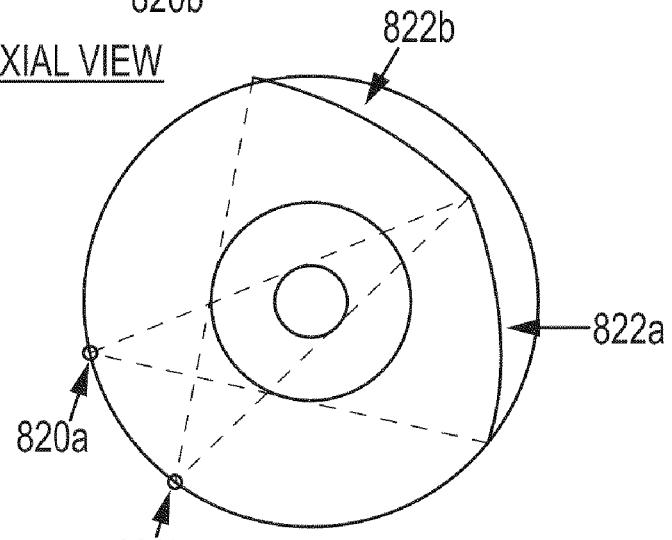
Figure 8B:
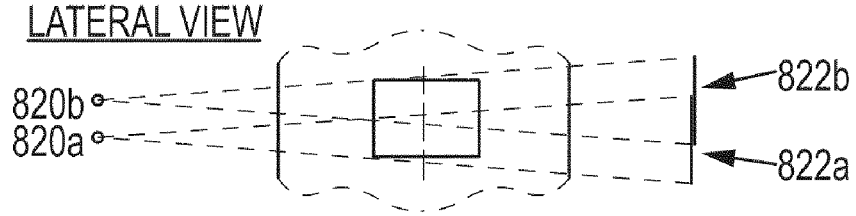

FIG. 8a illustrates a circular scanner 805 with one x-ray source 810 and FIG. 8b illustrates a staggered circular scanner 815 with two x-ray sources 820a and 820b according to an embodiment of the present inventions. In FIG. 8a, the axial extent of the region-of-interest (ROI) that can be captured by the Aquilion ONE is used as baseline for FIG. 8b. In the Aquilion ONE 805, the source-detector assembly 810 and 812 rotates around an axis called the axis, the z-axis, or the rotation axis, which is in the direction of the patient bed. In the staggered circular scanner 815, there is a first source-detector assembly 820a and 822a and a second source-detector assembly 820b and 822b rotating simultaneously around the axis. The two sources 820a and 820b are at different positions along the z-axis relative to the Aquilion ONE source 810, in which one of the sources is positioned at a lower z than the Aquilion source while the other source is at a higher z. The result of rotation of the two sources 820a and 820b is a vertex path comprising two circles (or segments of circles). The two sources 820a and 820b are also at different polar angle positions relative to the Aquilion ONE source 810. In one embodiment, the angular separation between the two sources is about 30 degrees which give ample space to place the two x-ray tubes of the sources 820a and 820b. The x-ray detector 822a and 822b associated with each source 820a and 820b is only about half the size of the Aquilion ONE detector 810 in the z direction, and is also shorter in angular coverage. Transaxially, the detector 822a and 822b associated with each source 820a and 820b is just wide enough to include all ray-sums through a central ROI on one side and to see the edge of the Aquilion ONE field-of-view (FOV) in the other direction.

In the example shown in FIG. 8b, each source 820a and 820b emits a beam of x-ray radiation that passes through a region-of-interest and is detected by a corresponding one of the x-ray detectors 822a and 822b, respectively. The lateral views of the CBs in FIGS. 8a and 8b show that the CB for each source 820a and 820b is significantly smaller than the CB for the Aquillion ONE source 810.

The staggered circular scanner 815 may comprise a rotatable frame or gantry 850 on which the source-detector assemblies are mounted. The gantry 850 may rotate about the rotation axis. The two sources 820a and 820b are angularly offset from one another (e.g., 30 degrees) around the rotation axis and axially offset from each other along the rotation axis, as discussed above. Each x-ray detector 822a and 822b is situated opposite the corresponding source 820a and 820b to detect x-ray radiation emitted from the corresponding source 820a and 820b. Each x-ray detector 822a and 822b may comprise rows of detector elements.

Each x-ray detector 822a and 822b has a curvilinear long axis 824a and 824b oriented along the rotation direction and a short axis transverse to the long axis 824a and 824b. Adjacent edges 828a and 828b of the x-ray detectors 822a and 822b substantially parallel to the short axes are positioned substantially next to each other so that the adjacent edges 828a and 828b are not substantially spaced from each other, as shown in FIG. 8b. In addition, the x-ray detectors 822a and 822b are angularly offset from one another around the rotation axis and axially offset from each other along the rotation axis.

During operation, the gantry 850 may be rotated by a motor to rotate the two source-detector assemblies about the rotation axis. The two source-detector assemblies obtain CB data on two parallel circular trajectories, each circular trajectory corresponding to one of the source-detector assembles. This allows CT imaging over a larger volume using smaller CBs and without requiring axial motion. The source-detector assemblies may be rotated 360 degrees for a complete circular scan or less than 360 degrees (e.g., 240 degrees) for a segment circular scan. CB data collected during the scan may be processed by an image processor into a CT image of the region-of-interest.

Figure 8C:
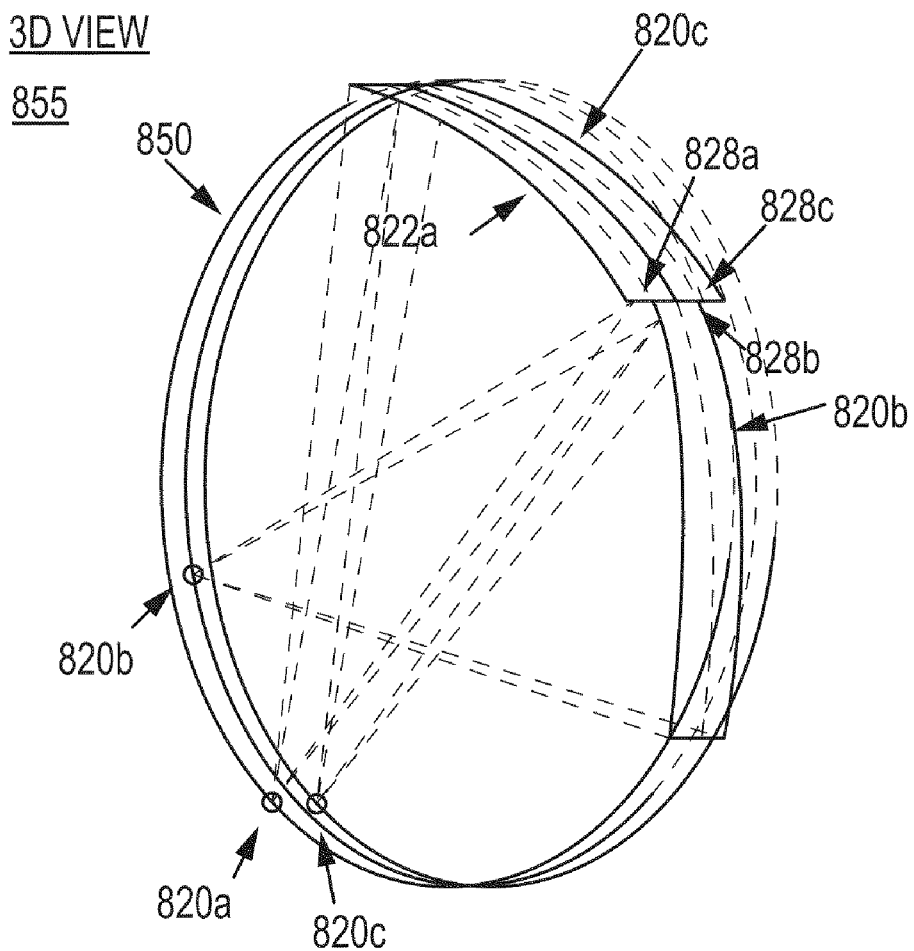
FIG. 8c shows a staggered circular scanner with three sources according to an embodiment of the present inventions.
Figure 8C:
Figure 8D:
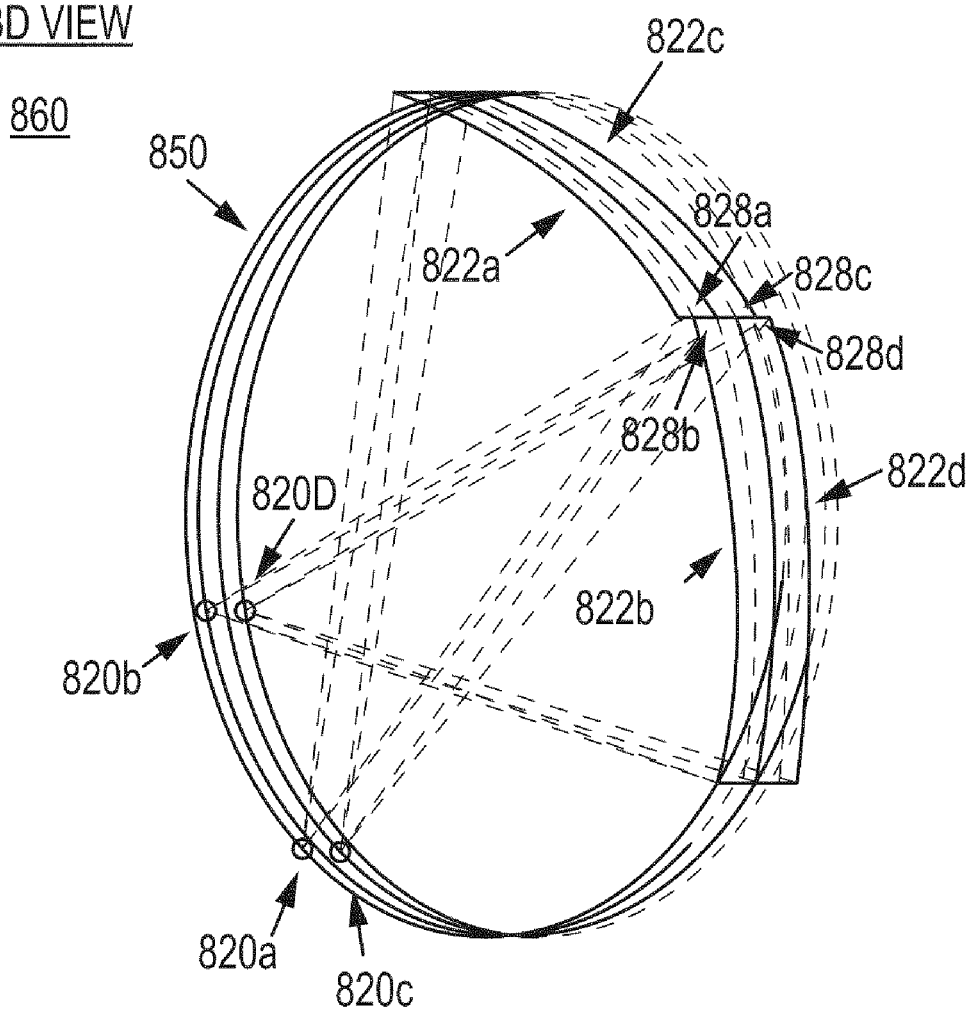
FIG. 8d shows a staggered circular scanner with four sources according to an embodiment of the present inventions.
Figure 8D:
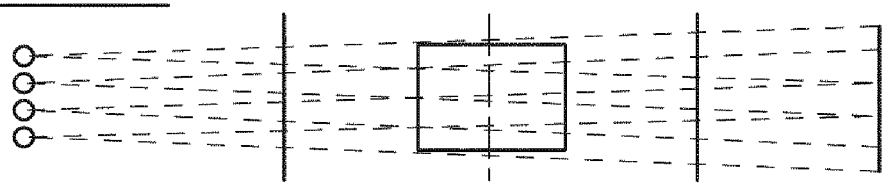

FIG. 8c illustrates a staggered circular scanner 855 with three sources 820a-820c and FIG. 8d illustrates a staggered circular scanner 860 with four sources 820a-820d according to embodiments of the present inventions. It can be seen that the adopted approach is to stack two source-detector assemblies one above the other. From a practical point of view, this stacking could be achieved by placing one tube upside-down relative to the other. An alternative approach would be to put the two tubes at different distances from the rotation axis. The first approach is used for purposes of discussion, as we do not think that this aspect of the problem has much impact on the evaluations discussed below.

In the example in FIG. 8c, each source 820a-820c emits a beam of x-ray radiation that passes through a region-of-interest and is detected by a corresponding one of the x-ray detectors 822a-822c, respectively. A comparison of the lateral views in FIGS. 8a and 8c show that the CB for each source 820a-820c is significantly smaller than the CB for the Aquillion ONE source 810.

The staggered circular scanner 855 may comprise a rotatable frame or gantry 850 on which the source-detector assemblies are mounted. The gantry 850 may rotate about the rotation axis. The first and third sources 820a and 820c are angularly aligned with one another and angularly offset from the second source 820d (e.g., 30 degrees) around the rotation axis. The sources 820a-820c are axially offset from one another other along the rotation axis. Each x-ray detector 822a-822c is situated opposite the corresponding source 820a-820c to detect x-ray radiation emitted from the corresponding source 820a-820c.

Each x-ray detector 822a-822c has a curvilinear long axis oriented along the rotation direction and a short axis transverse to the long axis. The curvilinear long axes are shown as dashed lines running through the detectors in FIG. 8c. Edges 828a and 828c of the first and third detectors 822a and 822c, respectively, are positioned substantially next to and adjacent to edge 828b of the second detector 822b, as shown in FIG. 8c. A center of the edge 828b of the second detector 822b is positioned approximately between the edges 828a and 828c of the first and second detectors 822a and 822c, respectively. Each edge 828a-828c is orientated parallel to the corresponding short axis. In addition, the first and third detectors 822a and 822c are angularly aligned with one another and both are angularly offset from the second detector 822b. The detectors 822a-822c are axially offset from one another.

During operation, the three source-detector assemblies may be rotated about the rotation axis obtain CB data on three parallel circular trajectories, each circular trajectory corresponding to one of the source-detector assembles.

In the example in FIG. 8d, each source 820a-820d emits a beam of x-ray radiation that passes through a region-of-interest and is detected by a corresponding one of the x-ray detectors 822a-822d, respectively. A comparison of the lateral views in FIGS. 8a and 8d show that the CB for each source 820a-820d is significantly smaller than the CB for the Aquillion ONE source 810.

The staggered circular scanner 860 may comprise a rotatable frame or gantry 850 on which the source-detector assemblies are mounted. The gantry 850 may rotate about the rotation axis. The first and third sources 820a and 820c are angularly aligned with one another and the second and fourth sources 820b and 820d are angularly aligned with one another. The pair of first and third sources 820a and 820c are angularly offset from the pair of second and fourth sources (e.g., 30 degrees) around the rotation axis. Thus, axially adjacent sources 820a-820d (e.g., the first and second sources 820a and 820b) along the rotation axis are angularly offset from one another. The sources 820a-820d are axially offset from one another other along the rotation axis. Each x-ray detector 822a-822d is situated opposite the corresponding source 820a-820d to detect x-ray radiation emitted from the corresponding source 820a-820d.

Each x-ray detector 822a-822d has a curvilinear long axis oriented along the rotation direction and a short axis transverse to the long axis. The curvilinear long axes are shown as dashed lines running through the detectors in FIG. 8d. Edges 828a and 828c of the first and third detectors 822a and 822c, respectively, are positioned substantially next to and adjacent to edge 828b of the second detector 822b, as shown in FIG. 8d. A center of the edge 828b of the second detector 822b is positioned approximately between the edges 828a and 828c of the first and third detectors 822a and 822c, respectively. Similarly, edges 828b and 828d of the second and fourth detectors 822b and 822d, respectively, are positioned substantially next to and adjacent to the edge 828c of the third detector 822c, as shown in FIG. 8d. A center of the edge 828c of the third detector 822c is positioned approximately between the edges 828b and 828d of the second and fourth detectors 822b and 822d, respectively. Each edge 828a-828c is orientated parallel to the corresponding short axis.

Further, the first and third detectors 822a and 822c are angularly aligned with one another and the second and fourth detectors 822b and 822d are angularly aligned with one another. The pair of first and third detectors 822a and 822c are angularly offset from the pair of second and fourth detectors 822b and 822d. The detectors 822a-822d are axially offset from one another.

In the example shown in FIG. 8, the angular positions of the sources 820a-820d along the rotation axis alternate between a first angular position and a second angular position that are offset from one another (e.g., 30 degrees). The first and third detectors 820a and 820b are aligned with the first angular position and the second and fourth detectors 820c and 820d are aligned with the second angular position. The angular offset between two axially adjacent sources may be less than 60 degrees, less than 45 degrees, or less than 30 degrees.

During operation, the four source-detector assemblies may be rotated about the rotation axis obtain CB data on four parallel circular trajectories, each circular trajectory corresponding to one of the source-detector assembles.

Staggered circular scans according to embodiments of the present inventions include one or more of the following advantages: (i) they allow simultaneous data collection over several circular trajectory with no overlap in the measurements, which would affect reconstruction stability, and with, of course, the desired reduction in cone angle, (ii) since each x-ray source is associated with an individual detector, a perfectly-aligned anti-scatter grid may be placed in front of each detector to block the scattered radiation coming from its x-ray source, (iii) the costs in additional sources is compensated by a reduction in the number of detector elements, which may range from about 30 to 40%, independently of the number of sources, and (iv) the costs in additional sources is also compensated by allowing the use of a tube with lower anode angle, providing more power and being thus of lower cost at equal power, since the required cone angle for each source is smaller. A weakness of staggered circular scans is cross-scatter from one source towards the detector of another source.

Figure 9:
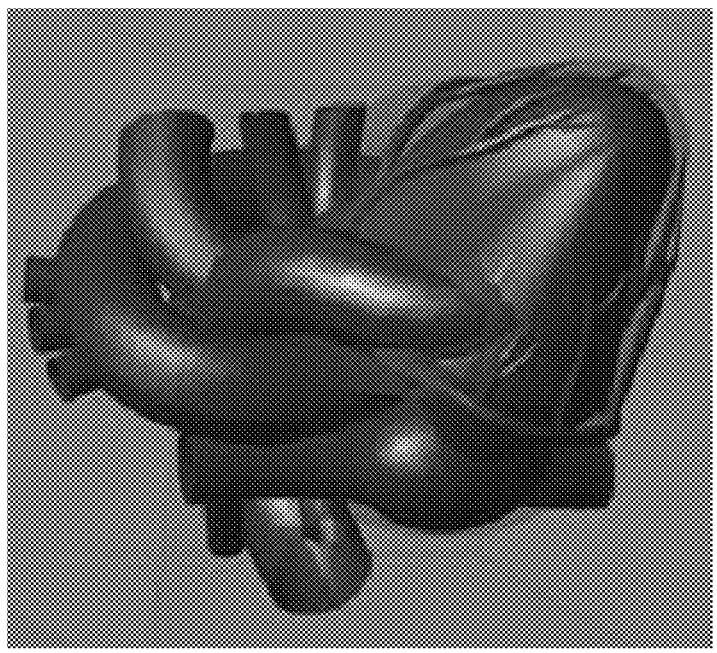
FIG. 9 shows a comparison of a UCAIR heart phantom and CT scans used for the development of the phantom.
Figure 9:

An evaluation of the impact of CB artifacts using an anthropomorphic heart phantom has been performed. The development of this phantom, called the UCAIR heart, was based on various sources of anatomical information and performed under the direction of the P.I. In the first stages of development, the primary sources of information were a physical heart model (Denoyer-Geppert Science Co., Skokie, Ill.), images from cardiac anatomy books and the dissection of a pig's heart. As the refinement of the model progressed, however, images from the Visible Human Project (both anatomical and CT images) and clinical CT images of a patient were used heavily to ensure consistency with a real human heart. FIG. 9 demonstrates the anthropomorphic accuracy of the UCAIR heart. FIG. 9 shows a comparison between the UCAIR heat and a CT scan used for its development; (top) coronal slice, (middle) sagitial slice and (bottom) transverse slice. Abbreviations in FIG. 9 are as follows: aorta (A), pulmonary trunk (PT), left ventricle (LV), left atrium (LA), right ventricle (RV), right atrium (RA), mitral valve (MV) and papillary muscle (PM). The specifics of the UCAIR heart can easily controlled to generate various heart models as needed for ROC based image quality assessment. FIG. 9 also shows a 3D rendering of the UCAIR heart with all cardiac muscles transparent so that the arteries can be visualized.

FIG. 10 below shows reconstruction results from a circular scan in the Aquilion ONE geometry. FIG. 10 shows some axial slices and MIP (maximum intensity projection) images, which are typically used to evaluate the presence or absence of a stenosis. These results demonstrate that CB artifacts with a full scan already affect the inspection of coronary arteries, and that CB artifacts with a short scan can have a very negative effect on image quality.

More particularly, in FIG. 10, the three images on the left are reconstructions from (top) slice-by-slice fan-beam data, (middle) full-scan circular CB data, and (bottom) short-scan circular CB data. The top image may be used as ground truth. The four images on the right are MIP images over a segment of the posterior descending artery (PDA). The images in the bottom row are obtained when the circular scan is centered on the artery, while the two images in the top row are obtained when the circular scan is 4 cm away from the artery. In each row, the left image is from full-scan data and the right image from short-scan data. The scale is in HU.

Figure 11:
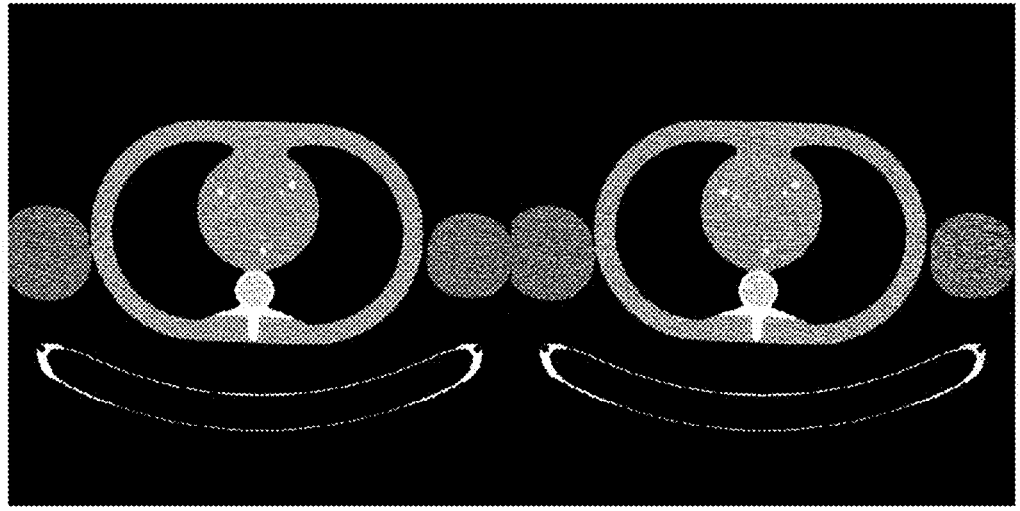
FIG. 11 shows reconstruction from real fan-beam data of a QRM phantom.
Figure 17:
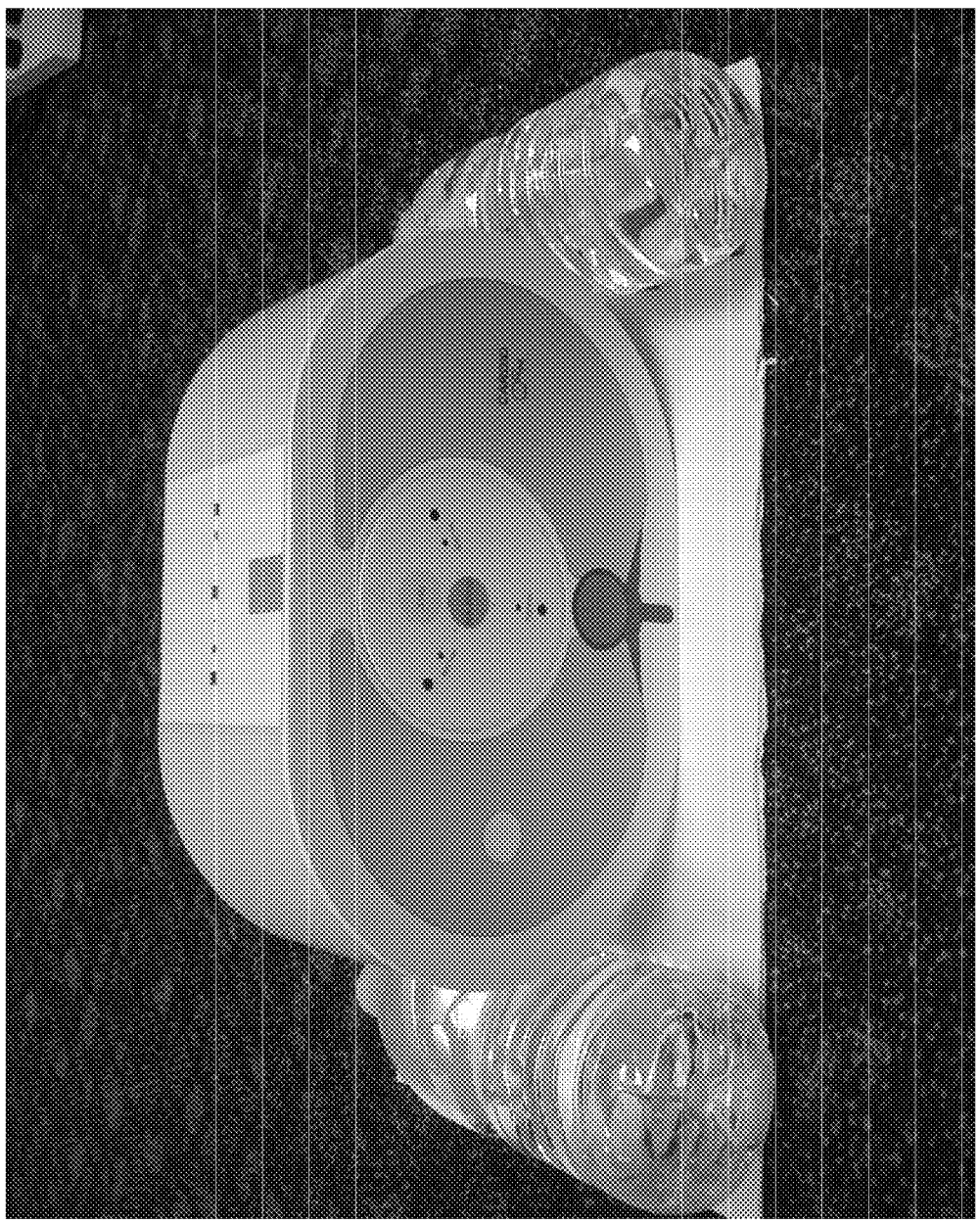
FIG. 17 shows an anthropomorphic cardio phantom from QRM.

To demonstrate the ability to process real data from a commercial CT scanner, projections of the QRM phantom (shown in FIG. 17) were collected using a Siemens Sensation 64. This phantom is used for the assessment of all kinds of image quality parameters in cardiac CT in an anthropomorphic environment. It is made of materials that attenuate X-rays like bones, lungs and tissues. Fan-beam data of this phantom was collected and two FBP reconstructions were performed, one conventional and one using a new weighting strategy described below, the results of which are given in FIG. 11. In FIG. 11, reconstruction from real fan-beam data of the QRM phantom. Left: conventional fill scan FBP reconstruction. Right: reconstructions obtained using the new fan-beam algorithm, which allows accurate handling of offset data with temporal resolution of a short-scan in the central ROI. See FIG. 17 for a picture of the QRM phantom.

Figure 12:
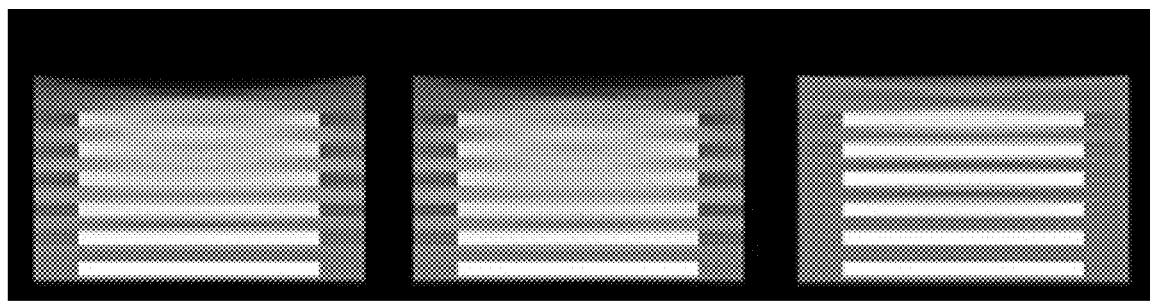
FIG. 12 shows reconstruction of a disk phantom using a short-scan FDK approach.

An experiment with a disk phantom is discussed below. As discussed above, some algorithms can perform better than others in terms of CB artifacts, although there may be a limit to how much image quality can be improved using algorithm development. A new method, called the factorization method, according to an embodiment of the present inventions comes close to reaching the optimal achievable image quality. FIG. 12 shows reconstructions of a disk phantom from a circular short scan, as obtained using this method. For comparison, FIG. 12 also shows the results obtained with two alternative methods: a commercially-used method and another method that was proposed recently and performs better than the commercially-used method in certain scenarios. More particularly, FIG. 12 shows reconstruction of a disk phantom using (left) the short-scan FDK approach, which is typically used in commercial systems, (middle) the ACE method, (right) the factorized method.

Another concern is to develop preliminary data that characterize the performance of staggered circular scans for coronary CTA. If these data give strong support for staggered circular scans, further assessment may be considered. This further assessment could first require a physical implementation of the data acquisition scheme, and the assistance and expertise of a CT manufacturer.

For all simulations, the following assumptions were made regarding the data acquisition geometry: (i) the detector paired to each source will be drawn on a cylindrical surface of radius $D=104$ cm centered on the line parallel to the rotation axis through the source position, (ii) the distance from each x-ray source to the rotation axis will be $R=57$ cm, (iii) the detector elements will be square, of side $\Delta=0.0912$ cm, so that a resolution of 0.05 cm may be targeted at field-of-view (FOV) center, (iv) the FOV diameter will be 25 cm, (v) a total of 2320 projections will be available over each 360 degree rotation, and (vi) the rotation speed will be of 250 ms per turn. All these parameters are consistent with current CT technology. The above parameters and geometries are merely exemplary, and other embodiments can have different parameters and geometries.

The region-of-interest (ROI) is viewed as a cylinder of radius of 9 cm, which largely encompasses the heart and surrounding vessels. And the detector coverage is assumed to be large enough to cover the same axial extent as the Aquilion ONE, as depicted in FIGS. 8a-8d. In practice, the heart could be centered in the ROI using two topograms, or scout views, at 90 degrees from each other to define and apply appropriate centering shifts to the patient bed.

Regarding motion, two assumptions are made. First, it is assumed that all structures outside the ROI are stationary over the 250 ms that are needed to collect data over 360 degrees. The ROI is large enough to include all large blood vessels. Second, it is assumed that all motion inside the ROI can be frozen over the 167 ms that are needed to collect data over 240 degrees. The validity of this second assumption depends of course on the heartbeat rate. Experience shows that cardiac images are essentially free of motion artifacts when the measurements associated to these images are centered on a slow motion phase of the heart cycle (end-diastolic or end-systolic) with a margin of ±15% of the heart cycle. Hence, heartbeat rates of up to 120 bpm can be accommodated with our assumption. Given these two assumptions and the fact that beat-to-beat variability is not a concern since the data acquisition is completed within a single heartbeat, it is believed that motion effects can be safely neglected, and therefore motion will not be included in our first-assessment of staggered circular scans.

At least two types of reconstruction algorithms can be used that differ from each other by the amount of projection coverage needed. The first type assumes that the CB projections are collected over 360 degrees, while the second type assumes that only projections over 240 degrees are available. The second type is more attractive in terms of dose, but also more complicated in terms of image reconstruction. In the first type, attention is given to not using ray-sums that pass through the ROI when these raysums originate from the last 120 degrees. This way a temporal resolution of 167 ms inside the ROI can be guaranteed. Two approaches will be investigated for each type of algorithm: filtered backprojection (FBP) methods based on Parker weighting, and methods based on differentiated-backprojection (DBP) and inverse Hilbert transform, like the factorization method. In any case, the investigation can be initiated with an analysis of a 2D reconstruction problem, namely how to perform reconstruction from fan-beam (FB) projections measured in the plane of the trajectory of one of the x-ray source. This initial investigation is expected to provide significant insight on how to best achieve the 3D reconstruction, and also will lead easily to initial 3D reconstruction algorithms by applying the principles of the FDK algorithm.

Figure 13:
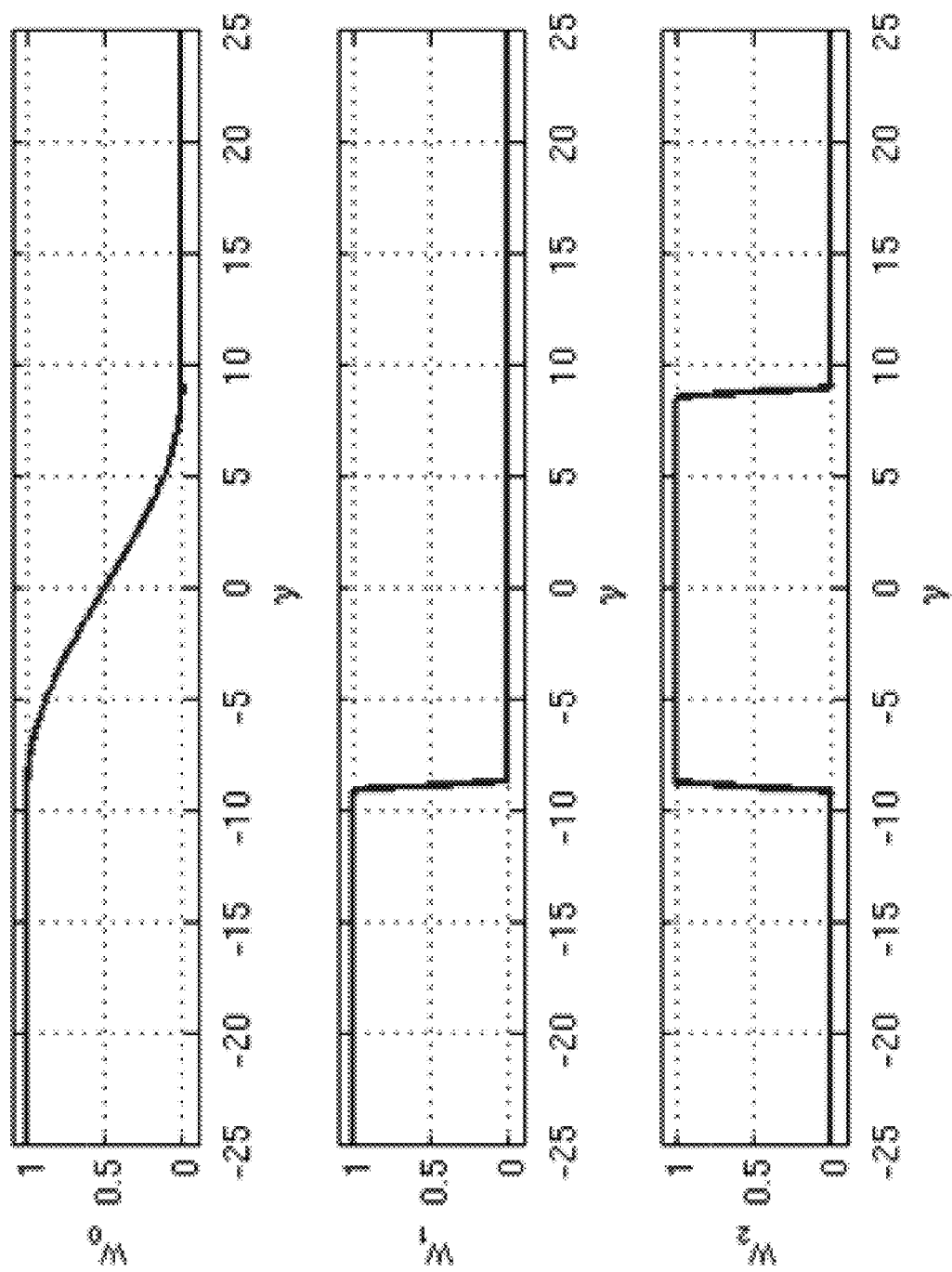
FIG. 13 shows plots of various weighting function useful for fan-beam FBP reconstruction with offset detector.

Solution of the 2D FB problem has been initiated, and the first observations are described below, which shows that the methodology is sound. Focus was mostly directed to the first type of algorithms. First, it is noted that each FB projection is truncated in a way that reminds one of full-scan tomography with offset detector, which has been previously suggested for FOV increase. For this problem, Cho et al. found that the truncation issue could be accurately handled by performing a conventional full-scan FBP reconstruction with pre-weighting of each projection with a view-independent weight w0 similar to that plotted in the top graph of FIG. 13. This knowledge appeared to be useful to us. However, w0 gives uneven contributions to the ray-sums through the ROI, which are each measured twice in a 360-degree acquisition. It has been found that using w1+0.5 w2, with w1 and w2 defined as shown in FIG. 13 (shown in the middle and the bottom graphs, respectively) uniformly weights the contribution of all ray-sums through the ROI. At first glance, it may seem like this finding was of little use for our needs. However, it paid off by giving a clearer insight into the problem. From there, it was found that using w1+w2·wP where wP is the weight of Parker for a short-scan of 240 degrees yields an accurate FBP reconstruction formula that never uses ray-sums through the ROI that originate from the projections measured over the last 120 degrees. A preliminary testing of this discovery was then performed. See FIG. 14. Two simple thorax phantoms were designed that differ from each other only by the orientation of ellipses inside the heart and performed first reconstruction of these two phantoms without and with Poisson noise added to the data using w1+0.5 w2 as pre-weighting factor to account for the offset detector; the results are on the top row. Next, the fan-beam projections of the first phantom (the one with vertical inner ellipses) were corrupted by replacing the last 120 degrees of data by the projections of the second phantom; this substitution simulates an (unlikely) sudden, large motion inside the ROI. Then, reconstruction of the corrupted data was performed using both w1+0.5 w2 and w1+w2·wP as pre-weighting factors. As expected, the former weight yield poor result. On the other hand, the second weight performed exactly as hoped, yielding no artifacts from the data corruption inside the ROI, and even outside. Of course, noise is increased inside the ROI since the investigation was essentially aimed at performing a short-scan type of reconstruction inside the ROI. These results demonstrate that reconstructions with a temporal resolution of 167 ms can be effectively performed while using data from 360 degrees.

Figure 14:
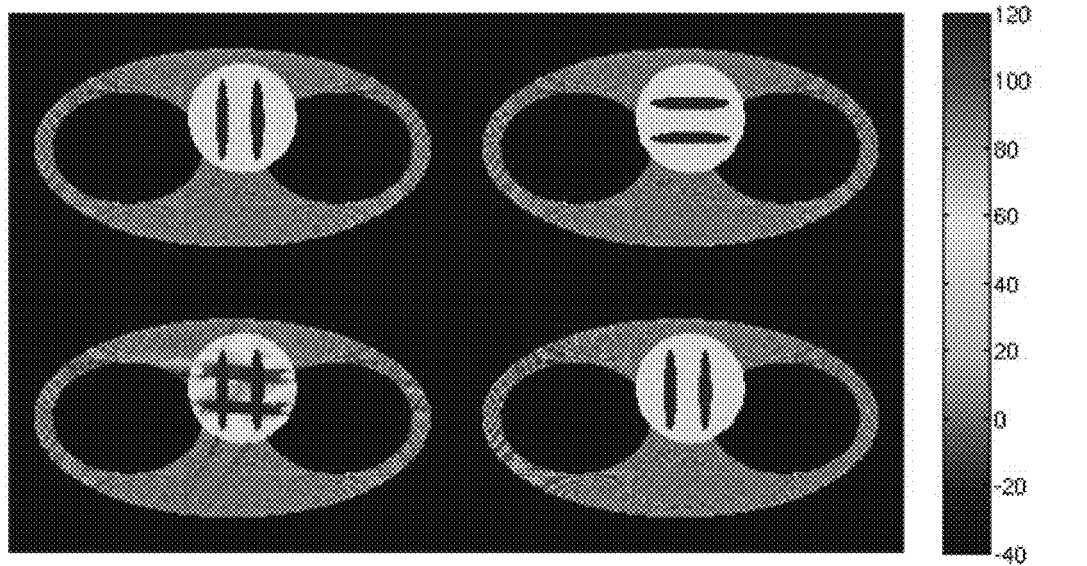
FIG. 14 shows fan-beam FBP reconstruction results with detector offset for staggered circular scans according to embodiments of the present inventions.
Figure 14:
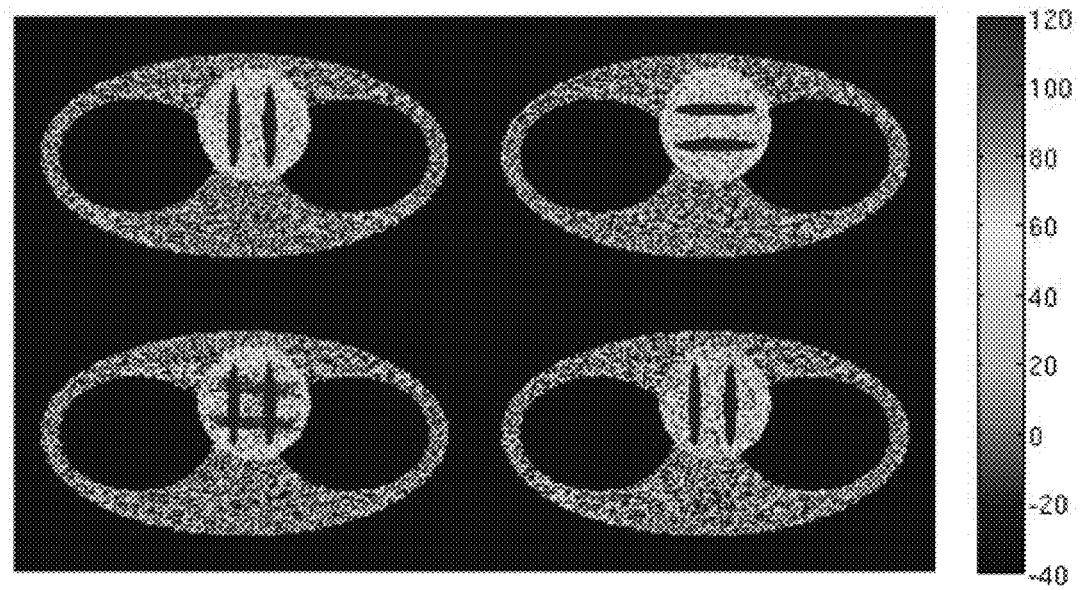

More particularly, FIG. 14 shows fan-beam FBP reconstruction results with detector offset as in staggered circular scans, obtained using two pre-weighting functions. The left set of four images is without noise, while the right set is with added Poisson noise corresponding to the emission of 400,000 photons per ray. The colorbar is in HU. In each set of four images, the bottom two images are with corrupted data, with the right image obtained using weighting and w1+w2·wP.

The development of a FB reconstruction algorithm of the second type has been investigated, and it was been discovered that the data obtained over 240 degrees is just sufficient for accurate reconstruction inside the ROI. It turns out that the reconstruction problem can be handled with the theory we developed, giving us strong hopes that data over more than 240 degrees may not be needed, which would be advantageous in terms of dose.

As already mentioned above, the entirety of aim 2 will be achieved using computer simulations. An important component of comparative evaluation is objective task-based assessment of image quality. Given that primary focus on coronary CTA, the task is identified as the detection of stenosis in coronary arteries. Imaging performance can be evaluated for this task using ROC-based human observer studies from computer-simulated reconstructions of anthropomorphic phantoms.

Another component of comparative evaluation is the characterization of scatter and dose. One approach for this characterization is the use of Monte-Carlo transport of x-ray photons through voxelized phantoms. Monte-Carlo methods have become the standard method for dose evaluations in radiation therapy treatment and have been recently extended for evaluation of dose in CT, with successful experimental validation demonstrated. Monte-Carlo methods are also widely used for scatter evaluation.

Figure 15:
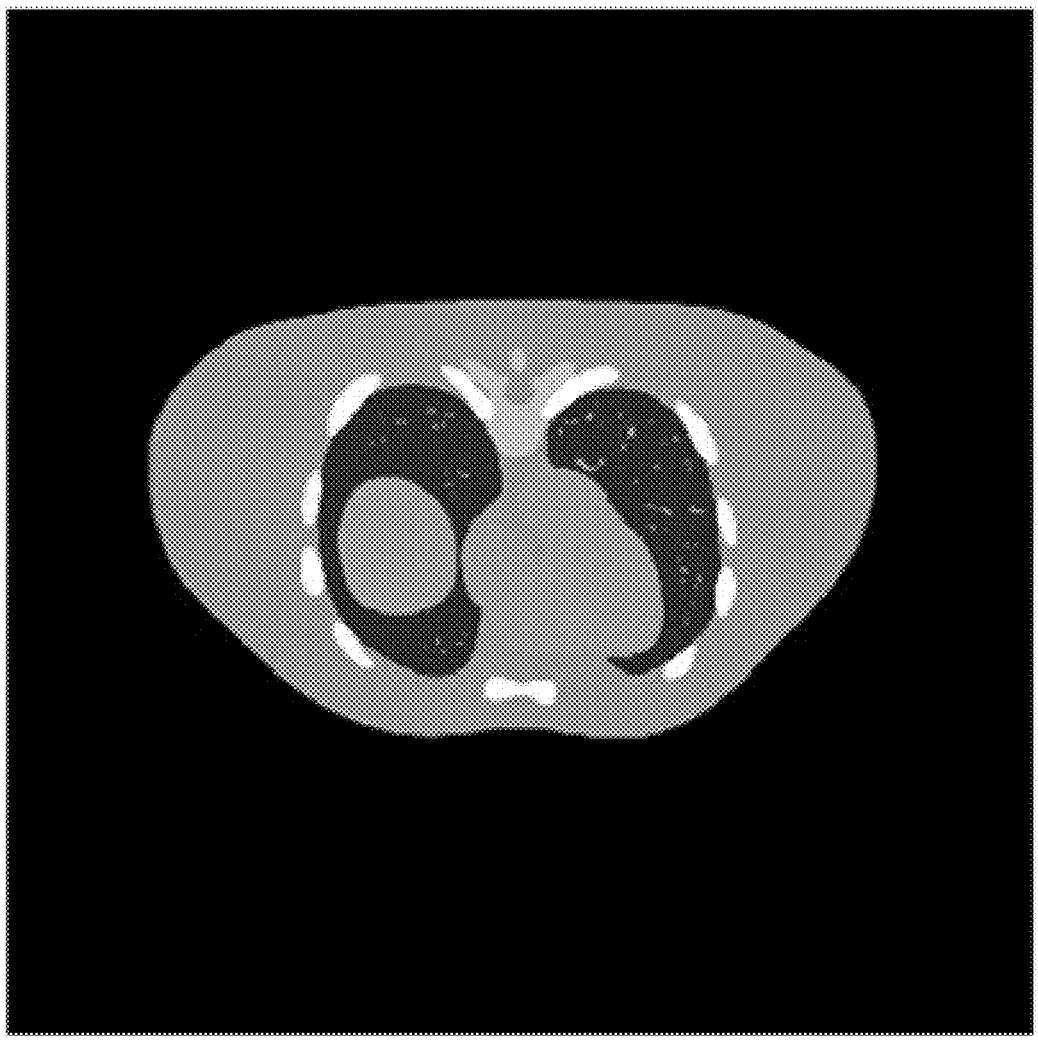
FIG. 15 shows axial and sagittal slices through the attenuation map of a NCAT phantom.
Figure 15:
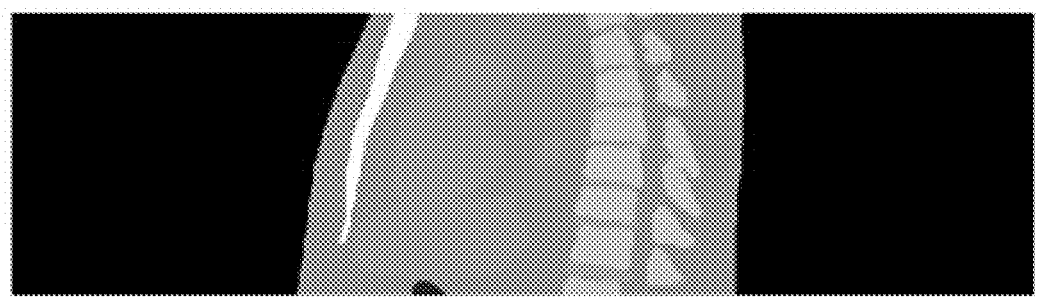

Also considered are two anthropomorphic phantoms for evaluations. The first phantom will be the NCAT phantom, which is based on NURBS functions and accurately model all organs within a patient body. This phantom was originally developed for investigations in nuclear medicine, namely in PET and SPECT. Its designer, Dr. Segars, is currently in the final phase of a funded NIH project that aims at refining the phantom to (i) allow accurate CT simulations, and (ii) include anatomic variability such as body size and gender that is crucially needed for objective assessment of image quality using observer studies. Software for simulations of voxelized versions of the NCAT phantom is freely distributed to academic institutions. This software has been run, the results of which we obtained are displayed in FIG. 15 and attest of the anatomic accuracy of the NCAT phantom.

At this stage, it is unclear whether or not the NCAT phantom will have enough flexibility in heart model and in placement of calcification and stenosis within the coronary arteries for our ROC-based observer study, as described below. If this is the case, this study can be performed using the phantom that results from combining together the NCAT phantom and the UCAIR heart using a precedency rule; the UCAIR heart was discussed above. This combination approach will offer us a highly-flexible anthropomorphic phantom, with the flexibility arising from control on the UCAIR heart.

Data simulations for the observer studies will be performed using the CTimulator, a software that was developed in collaboration with Philips. All simulations will include the geometrical effects of finite focal spot size with an anode angle of 9 degrees, finite detector size, and continuous (non-pulsed) x-ray emission. These effects are included according to the Lambert-Beer law for x-ray attenuation. Moreover, all simulations will be performed assuming a polychromatic emission of x-rays with tungsten target, using the well-benchmarked model of Tucker, Barnes and Chakraborty.

For image-quality evaluations, it is assume that a perfect scatter correction method is available, so that the only issue related to scatter is noise differences. To explain how these differences will be accounted for, an explanation of how noise is added to the data in the CTimulator is needed. To simplify the discussion, it is assumed here a monochromatic beam but polychromatism can be used. Basically, the CTimulator proceeds in four steps: (1) the raysum is computed from the phantom definition, (2) Lambert-Beer's law is applied to obtain from the raysum and a fixed number fin of incoming photons a number of transmitted photons, $n_{out}$, (3) $n_{out}$ is replaced by $n'_{out}$, which is one realization of a Poisson random variable of mean equal to $n_{out}$, (4) Beer-Lambert' s law is applied backward to obtain the noisy raysum from $n_{in}$ and $n'_{out}$. Consequently, the SNR is the square root of $n_{out}$. In the presence of scatter and of a scatter grid, the intensity of the primary beam is smaller and the noise is higher, so we need to adjust $n_{out}$ prior to replacing it by $n'_{out}$. $n_{out}$ is replaced by $\alpha$ $n_{out}$ with $\alpha=(p/n_{out})\times(1/(1+spr))$. In this expression, p is the intensity of the primary and spr is the scatter-to-primary ratio. The first factor in the expression of a accounts for the loss in primary due to the anti-scatter grid, while the second factor accounts for the noise increase due to scatter counts. $p/n_{out}$ and spr can be estimated using Monte-Carlo scatter-simulation program. Since such simulations can be time-demanding, it may be assumed that their dependence on heart model and location of stenoses and calcifications is negligible.

As discussed earlier, the human observer study will focus on the task of stenosis detection in the coronary arteries. The study will include 5 human observers: trained cardiac CT radiologists, Drs. Shaaban and Drs. Olpin, and three medical residents from the P.I.'s department of Radiology. The observers will evaluate images (readings) aiming at the comparison of four scenarios: (1) conventional circular CB tomography, (2) staggered circular scans with two sources, (3) staggered circular scans with three sources, and (4) staggered circular scans with four sources.

The observers will be asked to interpret reconstructions in a way that is reflective of the standard segmental classification of the American Heart Association. The coronary tree is divided into 15 segments for each of which the radiologist must chose between four diagnostics with a confidence level of 1 (non-reliable), 2 (moderately reliable) or 3 (reliable). The four diagnostics are (a) no stenosis, (b) stenosis less than 50% in size, (c) stenosis more than 50% in size, (d) not assessable. To imitate this task, the following instructions can be given to the observers: "rate each image according to your confidence that there is or there is not a stenosis present that is 50% or more in size". The rating scale will include 7 levels: (1) absolutely certain that there is not . . . , (2) fairly certain that there is not . . . , (3) somewhat certain that there is not, (4) equivocal, (5) somewhat certain that there is . . . , (6) fairly certain that there is . . . , (7) absolutely certain that there is . . . In this context, the "no stenosis" diagnostic would be reflected by a rating of (1) and the "not assessable" diagnostic by a rating of (4).

A common method used by the radiologist for examining a coronary segment is to use slab MIPs (maximum intensity projections), 3-5 mm thick, in planes that cover the entire segment. These slabs are similar to those shown above (FIG. 9), and recommendations have been published on how to find the proper planes for each segment. Accordingly, each image supplied to the observer will be a set of four MIPs for each segment. The MIPs will be at 0, 45, 90 and 135 degrees around the artery segment and will have a thickness directly proportional to the thickness of the coronary segment. Such a procedure has the advantage of not requiring the observers to be very familiar with the anatomy of the heart. As usual, the readings will take place in a darkened room, and the display monitor settings will be calibrated so that the gray scale provides a logarithmic-linear relationship. Moreover, to prevent fatigue the reading sessions will not last more than one to one and a half hour.

There are several factors that can affect stenosis detection. Three factors that are deemed relevant for study are: (a) the location and the thickness of the segment in which the stenosis appears, (b) the presence of a calcification near the stenosis, and (c) the body size. For the reasons explained above, heart motion is not included in these factors. The reading cases can include 2 settings, namely a medium body size and a large body size. For each setting, 5 different heart models are considered, in each of which 4 segments with a stenosis are selected, 2 with calcifications and 2 without calcifications. Among the other 11 segments, 7 can be discarded while the remaining four can be included in the study—2 with calcifications and 2 without. The total number of readings per scenario can thus be 2×5×8=80, and there can be the same number of actually positive and actually negative cases, which is ideal from a statistical viewpoint. Preliminary studies can be performed to gain insight on how to select the important readings, and thereby obtain sufficient statistical power with these 80 readings. Also, to prevent fatigue without advantaging a given scenario, the observations can occur in 3 to 4 sessions distributed over a period of 2 to 3 weeks with random shuffling of all segments across settings, heart models and scenarios.

The observers can be trained in two stages. First, the observers can be shown a series of normal and abnormal objects (not reconstructions) and asked to identify each object as normal or abnormal. This stage can be achieved until the observer correctly identifies 90% of objects shown, which may not be part of the studies. The second stage can involve (i) showing the observer several images (50% of normal and 50% of abnormal from each scenario), (ii) asking the observer to rate the image, and (iii) continuing until the performance of the observer stabilizes.

The analysis of results can be done with the assistance of Dr. Kadrmas who has wide experience in human observer studies. The figure-of merit resulting from the observer study can1 be the AUC, i.e., the area under the ROC curve. ROC curve fitting and statistical analysis can be performed using freely available software packages such as ROCFIT, CORROC, CLABROC, or MRMC. Paired statistical tests can be used as appropriate in order to maximize the statistical power of the study. ANOVA (analysis of variance) can be used to study inter-observer differences and differences between scenarios. Differences can be considered significant for $p<0.05$.

All scatter and dose evaluations can be performed using a software being developed by the P.I. This software is dedicated exclusively to our needs, namely x-ray CT imaging with energies between 3 kEv and 250 kEv. It is noted that there exist at least two freewares for Monte Carlo transport of particles through matter: Geant4 and MCNP. However, the wide range of transport problems that Geant4 and MCNP can handle render these softwares unwieldy for medical imaging applications, particularly in terms of detector geometry and phantom design. For this reason, imaging scientists in nuclear medicine have developed GATE as an interface to GEANT dedicated to their needs. The option of using GATE has been investigated but GATE is not well-designed for CT evaluations and significant effort would be needed to make it appropriate. Hence, software may be developed following the path of CT vendors and other academic sites.

Figure 16:
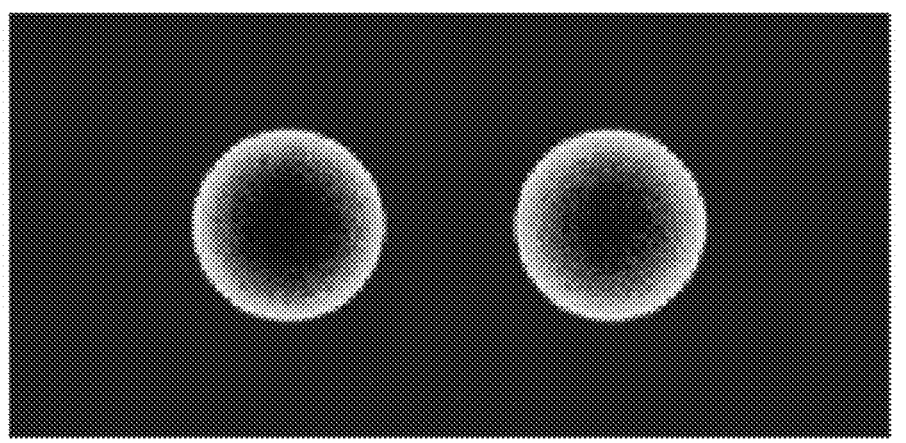
FIG. 16 shows first scanner simulation results.
Figure 16:
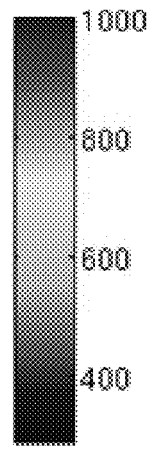
Figure 16:
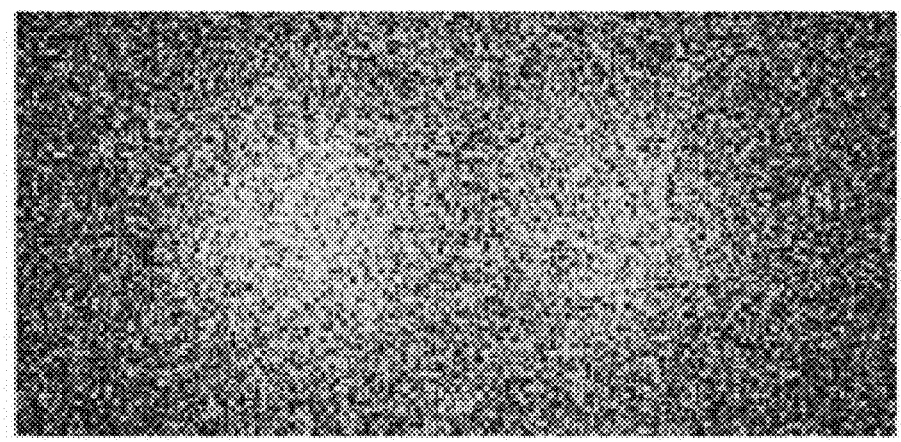
Figure 16:
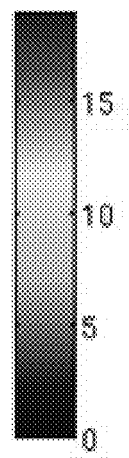

The development of a Monte Carlo program for transport of x-ray photons through matter follows the recommendations given in Report No 108 of NCRP. Briefly, photoabsorption, compton scattering and coherent scattering are modeled. The mass photoabsorption coefficents were obtained from the NIST database, while the differential cross sections were obtained using the atomic form factors and incoherent scattering functions tabulated by Hubbell. Differential cross sections were integrated to verify that they give the same absorption coefficient as in the XCOM database. Also, coherent scatter was not neglected because it plays a significant role in CT, since the detector is generally a good distance away from the scanned object and coherent scatter is mostly forward. Transport through a voxelized phantom was allowed that can be composed of up to 10 materials. The cross sections for each material were obtained by linear combination of cross sections for relevant atoms, using fraction-by-weights as combination factors. The materials are: liquid water, cortical bone, brain-matter tissue, adipose tissue, air, eye lens, blood, lung tissue, muscle and soft tissue. The fractions by weight were taken from ICRU-44. Transport is currently stopped when the photon has either scattered more than 10 times or when its energy is below 3 kEv; in either case it can be assumed the photon is then absorbed. First results obtained with our software are shown in FIG. 16. These were obtained for a detector with 120 rows and 200 elements per row, with a simple phantom consisting of two spheres parallel to the detector, assuming an emission of 1000 photons of energy 80 kEv towards each detector element.

The following tasks remain to be performed: (i) inclusion of fluorescence for large atomic numbers, (ii) inclusion of x-ray source spectrum, (iii) allowance for finite focal spot size with anode angle and continuous x-ray emission, (iv) transport through bowtie-filter and anti-scatter grid, (v) modeling of energy integrating detectors. For tasks other than the first task, the steps taken and described herein may be followed.

The scatter simulation program can be validated through comparisons with results from MCNP and from real projection measurements. These results can be obtained with the assistance of a long-time collaborator of the P.I., Dr. White, from the Idaho National Laboratory.

Scatter can be characterized for various anti-scatter grids, using grid parameters given in. One-dimensional and bi-dimensional grids can be both considered. Transport through the NCAT phantom can be used for this characterization, after attributing to each voxel of this phantom one specific material.

For this research, the dose evaluation can be restricted to energy deposition. This deposition can be obtained as a bypass product of the scatter simulation program, as described in. The deposition inside the entire volume and individually for the dose-sensitive organs near the heart (namely, the liver, the lungs and the bone marrow) can be considered. The phantom used for this evaluation can be the NCAT phantom.

Circular CB scans with any commercial CT scanner can be collected and anyone of the staggered circular scans can be simulated from these scan data, by truncating the measured projections on one side. It is proposed do so using two systems: a single-tube 64-slice system (namely, the Siemens Sensation 64) and a dual-tube 64-slice system (namely, the Siemens Definition). Measurements from these two scanners allows evaluation of a preferred reconstruction algorithm in two environments: without and with presence of cross scattered radiation. From a master research agreement with Siemens, software is available to read the data from the two systems.

For evaluations, the anthropomorphic cardio phantom from QRM, GmbH (Germany) can be used. Prior to beginning the evaluations, the phantom can be rendered more challenging, by adding a ribs cage to it, and by designing a new cardiac insert with embedded tubes mimicking vessels.

Three evaluations can be performed in each environment (without and with cross-scatter) and compared to results from a conventional circular short-scan. The first evaluation can amount to performing noise variance measurements in the ROI using repeated scans, with a water-filled cylinder in place of the cardiac insert. The second evaluation can amount to measuring the uniformity of reconstructed CT values in and the cross-section area of embedded tubes mimicking vessels inside the new cardiac insert; these measurements can also be performed with repeated scans, to establish the effect of noise on them. The third evaluation can be an ROC-based human observer study for detectability of a known signal inside a uniform background, placed near the center of the ROI. The known signal can be a small semi-high-contrast sphere, and the known background can be a water-filled cylinder, in which the sphere is embedded. The cylinder can replace the cardiac insert. The sphere can hang in the water thanks to a thin low-attenuation thread, as in the QRM anthropomorphic pulmo phantom. By slightly pushing the insert up or down, images without and with the sphere present can be generated.

General body imaging with a CT scanner is typically performed with patient bed translation, which yields wide axial coverage and also complete data allowing accurate reconstruction. As discussed above it is important to illustrate early that accurate general body imaging is feasible using a scanner designed to perform staggered circular scans. It is believed that accurate body imaging should be at least possible by translating the patient bed at a speed such that each source traces the same helix path relative to the patient. By combining the data from the various sources together, complete data can be obtained and thereby achieve accurate reconstruction. This option can be investigated and also identify if any the difficulties that arise when the helix pitch is selected otherwise. To speed-up the development of the reconstruction algorithm, approximate methods can be used instead of theoretically-exact methods. More specifically, developments can be restricted to extending the simple, straightforward FBP method that is currently implemented on Siemens scanners. Only subjective image quality evaluations can be performed for this fourth aim; these can be achieved using simulated data obtained from projections of the QRM cardio phantom (FIG. 17) collected on scanners.

It will be also appreciated by persons skilled in the art that numerous variations and/or modifications may be made to the specific embodiments disclosed herein, without departing from the scope or spirit of the disclosure as broadly described. The present embodiments are, therefore, to be considered in all respects illustrative and not restrictive of the present inventions.

What is claimed is:
1. A CT imaging system, comprising:
  a plurality of x-ray sources configured to rotate about an rotation axis, the x-ray sources each generating a beam of radiation, at least two of the plurality of x-ray sources being angularly offset from each other at discrete locations around the rotation axis and being axially offset from each other along the rotation axis;
  a plurality of x-ray detectors configured to rotate about the rotation axis in a rotation direction, each detector situated opposite an associated one of the plurality of x-ray sources and having (i) a curvilinear long axis oriented along the rotation direction, and (ii) a short axis that is transverse to the long axis, at least two of the plurality of detectors being angularly offset from each other at discrete locations around the rotation axis and being axially offset from each other along the rotation axis; and
  wherein adjacent edges parallel to the short axes of the at least two angularly offset x-ray detectors are not substantially spaced apart from each other.

2. The CT imaging system of claim 1, wherein the plurality of x-ray sources are configured to rotate along parallel circular trajectories.

3. The CT imaging system of claim 1, wherein at least two of the plurality of x-ray sources are angularly aligned with each other around the rotation axis.

4. The CT imaging system of claim 1, wherein two axially adjacent x-ray sources of the plurality of x-ray sources along the rotation axis are angularly offset from one another by 60 degrees or less.

5. The CT imaging system of claim 1, wherein two axially adjacent x-ray sources of the plurality of x-ray sources along the rotation axis are angularly offset from one another by 45 degrees or less.

6. The CT imaging system of claim 1, wherein angular positions of the plurality of x-ray sources alternate between a first angular position and a second angular position along the rotation axis.

7. The CT imaging system of claim 6, wherein the first angular position and the second angular position are offset by 60 degrees or less.

8. The CT imaging system of claim 6, wherein the first angular position and the second angular position are offset by 45 degrees or less.

9. The CT imaging system of claim 1, wherein a center of an edge of one of the plurality of x-ray detectors is positioned approximately equidistant and adjacent to an area between edges of two other x-ray detectors of the plurality of x-ray detectors.

10. The CT imaging system of claim 9, wherein the edge of the one of the plurality of x-ray detectors is not substantially spaced apart from the edges of the two other x-ray detectors of the plurality of x-ray detectors.

11. The CT imaging system of claim 1, wherein two axially adjacent x-ray sources of the plurality of x-ray sources along the rotation axis are angularly offset from one another by 30 degrees or less.

12. A CT imaging system, comprising:
a plurality of x-ray sources configured to rotate about an rotation axis, the x-ray sources each generating a beam of radiation, the plurality of x-ray sources being axially offset from one another along the rotation axis;
a plurality of x-ray detectors configured to rotate about the rotation axis in a rotation direction, each detector situated opposite an associated one of the plurality of x-ray sources and having a curvilinear long axis oriented along the rotation direction;
wherein two of the plurality of x-ray detectors share an edge parallel to the rotation axis, the edge joining adjacent portions of the two x-ray detectors; and
wherein at least two of the plurality of x-ray sources along the rotation axis are angularly offset from each other by 60 degrees or less.

13. The CT imaging system of claim 12, wherein the plurality of x-ray sources are configured to rotate along parallel circular trajectories.

14. The CT imaging system of claim 12, wherein the plurality of x-ray sources comprises at least four x-ray sources.

15. The CT imaging system of claim 12, wherein the axially adjacent x-ray sources are angularly offset from each other by 45 degrees or less.

16. The CT imaging system of claim 12, wherein the axially adjacent x-rays sources are angularly offset from one another by 30 degrees or less.

17. The CT imaging system of claim 12, wherein angular positions of the plurality of x-ray sources alternate between a first angular position and a second angular position along the rotation axis, the first and second angular positions being offset from each other by 60 degrees or less.

18. The CT imaging system of claim 17, wherein the first and second angular positions are offset by 30 degrees or less.

* * * * *